(12) United States Patent
DeVries et al.

(10) Patent No.: US 6,291,489 B1
(45) Date of Patent: Sep. 18, 2001

(54) PROCESS FOR SUBSTITUTED PYRIDINES

(75) Inventors: Keith M DeVries, Chester; Robert L. Dow, Waterford; Stephen W. Wright, Old Lyme, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/297,694

(22) PCT Filed: Nov. 3, 1997

(86) PCT No.: PCT/IB97/01367

§ 371 Date: May 5, 1999

§ 102(e) Date: May 5, 1999

(87) PCT Pub. No.: WO98/21184

PCT Pub. Date: May 22, 1998

Related U.S. Application Data

(60) Provisional application No. 60/030,880, filed on Nov. 14, 1996.

(51) Int. Cl.$^7$ .......................... C07D 213/75; A61K 31/44
(52) U.S. Cl. .............................................. 514/352; 546/312
(58) Field of Search .............................. 546/312; 514/352

(56) References Cited

U.S. PATENT DOCUMENTS

| | | | |
|---|---|---|---|
| 4,358,455 | 11/1982 | Atkinson et al. ..................... | 546/300 |
| 5,019,578 | 5/1991 | Fisher et al. ......................... | 514/275 |

FOREIGN PATENT DOCUMENTS

| | | |
|---|---|---|
| WO9429290 | 12/1994 | (WO) . |
| WO9529159 | 11/1995 | (WO) . |
| WO9635670 | 11/1996 | (WO) . |
| WO9635671 | 11/1996 | (WO) . |

OTHER PUBLICATIONS

J. Am. Chem. Soc. 1981, 103, 1271–1273.

Primary Examiner—Zinna Northington Davis
(74) Attorney, Agent, or Firm—Peter C. Richardson; Gregg C. Benson; Martha A. Gammill

(57) ABSTRACT

This invention relates to processes for preparing compounds of the formula (I)

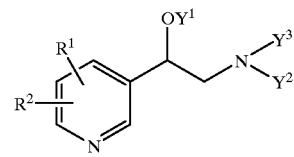

I and to processes for preparing certain intermediates of the formula

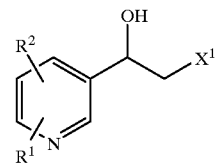

II$^A$ wherein $R^1$ is nitro, amino or protected amino; $R^2$ is H, fluoro, chloro $CF_3$, nitro, $(C_1-C_4)$alkyl, $(C_1-C_4)$alkoxy, amino or protected amino; and $X^1$ is OH or a suitable leaving group, used in that process. The invention also relates novel to compounds of the formulae (II).

60 Claims, No Drawings

PROCESS FOR SUBSTITUTED PYRIDINES

CROSS REFERENCE TO RELATED APPLICATIONS

This application is the national stage of International Application No. PCT/IB97/01367, filed Nov. 3, 1997, entitled "Process for Substituted Pyridines", which is a continuation of U.S. Provisional Application No. 60/030,880, filed Nov. 14, 1996, now abandoned.

BACKGROUND OF THE INVENTION

The present invention relates to certain compounds of the formula (II$^A$) depicted below, which are useful in the synthesis of certain β-adrenergic receptor agonists having the general formula (I):

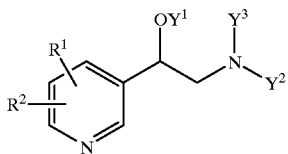

I where $R^1$ and $R^2$ are as defined herein for the compound of formula (II$^A$) hereinbelow and $Y^1$, $Y^2$ and $Y^3$ are chemical substituents which can be attached to the atoms to which they are attached. These substituents confer β-adrenergic receptor activity and as such the compounds of formula (I) have utility as hypoglycemic and antiobesity agents. Examples of such substituents and the resultant β-adrenergic receptor agonists can be found in PCT Publication No. WO 94/29290 published Dec. 22, 1994. The invention also relates to a process for synthesizing the compounds of formula (II) hereinbelow and to a process for synthesizing compounds of the formula (III), which are useful in the synthesis of the compounds of formula (I). The invention further relates to processes for synthesizing compounds of formula (I). The β-adrenergic receptor agonists also possess utility for increasing lean meat deposition and/or improving the lean meat to fat ratio in edible animals.

The β-adrenergic receptor agonists further possess utility in the treatment of intestinal motility disorders, depression, prostate disease, dyslipidemia, and airway inflammatory disorders such as asthma and obstructive lung disease.

The disease diabetes mellitus is characterized by metabolic defects in production and/or utilization of carbohydrates which result in the failure to maintain appropriate blood sugar levels. The result of these defects is elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type I diabetes, or insulin-dependent diabetes, is the result of an absolute deficiency of insulin, the hormone which regulates carbohydrate utilization. Type II diabetes, or non-insulin dependent diabetes, often occurs with normal, or even elevated levels of insulin and appears to be the result of the inability of tissues to respond appropriately to insulin. Most of the Type II diabetics are also obese.

The β-adrenergic receptor agonists effectively lower blood glucose levels when administered orally to mammals with hyperglycemia or diabetes.

The β-adrenergic receptor agonists also reduce body weight or decrease weight gain when administered to mammals. The ability of β-adrenergic receptor agonists to affect weight gain is due to activation of β-adrenergic receptors which stimulate the metabolism of adipose tissue.

β-Adrenergic receptors have been categorized into $β_1$-, $β_2$- and $β_3$-subtypes. Agonists of β-receptors promote the activation of adenyl cyclase. Activation of $β_1$-receptors invokes increases in heart rate while activation of $β_2$-receptors induces relaxation of skeletal muscle tissue which produces a drop in blood pressure and the onset of smooth muscle tremors. Activation of $β_3$-receptors is known to stimulate lipolysis (the breakdown of adipose tissue triglycerides to glycerol and free fatty acids) and metabolic rate (energy expenditure), and thereby promote the loss of fat mass. Compounds that stimulate β-receptors are, therefore, useful as anti-obesity agents, and can also be used to increase the content of lean meat in edible animals. In addition, compounds which are $β_3$-receptor agonists have hypoglycemic or anti-diabetic activity, but the mechanism of this effect is unknown.

Until recently $β_3$-adrenergic receptors were thought to be found predominantly in adipose tissue. $β_3$-receptors are now known to be located in such diverse tissues as the intestine (*J. Clin. Invest.*, 91, 344 (1993)) and the brain (*Eur. J. Pharm.*, 219,193 (1992)). Stimulation of the $β_3$-receptor has been demonstrated to cause relaxation of smooth muscle in colon, trachea and bronchi. *Life Sciences*, 44(19), 1411 (1989); *Br. J. Pharm.*, 112, 55 (1994); *Br. J. Pharmacol.*, 110, 1311 (1993). For example, stimulation of $β_3$-receptors has been found to induce relaxation of histamine-contracted guinea pig ileum, *J.Pharm.Exp.Ther.*, 260, 1, 192 (1992).

The $β_3$-receptor is also expressed in human prostate. Because stimulation of the $β_3$-receptor causes relaxation of smooth muscles that have been shown to express the $β_3$-receptor (e.g. intestine), one skilled in the art would predict relaxation of prostate smooth muscle. Therefore, $β_3$-agonists will be useful for the treatment or prevention of prostate disease.

Examples of β-adrenergic receptor agonists which can be synthesized using the compounds of formula (III) can be found in PCT Publication No. WO 94/29290 published Dec. 22, 1994, U.S. patent application Ser. No. 08/312,027 filed Sep. 26, 1994, PCT Application No. PCT/IB95/00344 filed May 10, 1995 and U.S. Provisional Application No. 60/015,216 filed Apr. 9, 1996, all of which are assigned to the assignee hereof.

With regard to the process of synthesizing a compound of formula (II) wherein X is OH, defined hereinbelow, of the present invention, the chemical literature teaches that addition of osmium tetroxide to olefins, including the olefin moiety of allylic and styryl compounds, results in the addition of two OH groups to the double bond, with one OH group being added to each carbon atom constituting the double bond. (see *Advanced Organic Chemistry*, March, John Wiley and Sons, NY, N.Y., 1985, 3rd Ed.) Two OH groups can also be added to double bonds by reacting the compound containing the double bond with (i) hydrogen peroxide and catalytic amounts of osmium tetroxide, (ii) alkaline potassium permanganate; (iii) hydrogen peroxide and formic acid; or (iv) iodine and silver benzoate. These methods all suffer from the drawback that they do not react stereospecifically with a prochiral carbon atom of the double bond to create an optically active dihydroxy compound.

U.S. Pat. No. 5,019,578 discloses a process for preparing epoxy-pyridine compounds. That process involves hydroxy bromination of a 5-ethenyl pyridine derivative followed by cyclization to the epoxide and suffers from the disadvantage that the bromohydrin is prepared as a racemic mixture.

SUMMARY OF THE INVENTION

This invention provides compounds of the formula

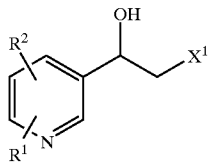

II$^A$ wherein: R$^1$ is selected from the group consisting of nitro, amino and protected amino; R$^2$ is selected from the group consisting of H, fluoro, chloro, CF$_3$, nitro, (C$_1$–C$_4$)alkyl, (C$_1$–C$_4$)alkoxy, amino and protected amino; X$^1$ is OH or a suitable leaving group; racemic mixtures thereof; R enantiomers thereof, wherein said R enantiomers are essentially free of their corresponding S enantiomers; and S enantiomers thereof, wherein said S enantiomers are essentially free of their corresponding R enantiomers thereof.

This invention particularly provides a compound as described in the immediately preceding paragraph wherein X$^1$ is OH.

This invention more particularly provides a compound as described in the immediately preceding paragraph wherein said protected amino, for each occurrence, is independently selected from the group consisting of (C$_1$–C$_8$)alkylamino, —NR$^3$CO(CH$_2$)$_p$R$^0$, —NR$^3$CO$_2$R$^0$ and —NR$^3$SO$_2$(CH$_2$)$_p$R$^0$; R$^3$, for each occurrence, is independently H or (C$_1$–C$_6$)alkyl; R$^0$, for each occurrence, is independently C$_1$–C$_{10}$ alkyl, phenyl or phenyl independently substituted by one to three (C$_1$–C$_4$)alkyl, (C$_1$–C$_4$)alkoxy or halo; and p is 0, 1 or 2.

This invention still more particularly provides compounds as described in the immediately preceding paragraph wherein R$^2$ is H.

This invention still more particularly provides compounds as described in the immediately preceding paragraph wherein R$^1$ is amino, —NR$^3$CO(C$_1$–C$_{10}$)alkyl, —NR$^3$CO$_2$(C$_1$–C$_8$)alkyl or —NR$^3$CO(CH$_2$)$_p$R$^0$.

This invention still more particularly provides compounds as described in the immediately preceding paragraph wherein R$^1$ is amino or —NR$^3$CO(C$_1$–C$_{10}$)alkyl.

This invention still more particularly provides N-(5-(1,2-dihydroxyethyl)-pyridin-2-yl)-acetamide. Still further, this invention provides the R enantiomer of N-(5-(1,2-dihydroxyethyl)-pyridin-2-yl)-acetamide, essentially free of its corresponding S enantiomer. Still further, this invention provides the S enantiomer of N-(5-(1,2-dihydroxyethyl)-pyridin-2-yl)-acetamide, essentially free of its corresponding R enantiomer.

This invention also provides compounds of formula (II$^A$) above wherein X$^1$ is a leaving group, said leaving group is organosulfonyloxy and said organosulfonyloxy is methanesulfonyloxy, benzenesulfonyloxy, p-toluenesulfonyloxy, p-nitrobenzenesulfonyloxy or m-nitrobenzenesulfonyloxy.

This invention more particularly provides those compounds as described in the immediately preceding paragraph wherein said organosulfonyloxy is p-toluenesulfonyloxy.

This invention more particularly provides compounds as described in the immediately preceding paragraph wherein said protected amino, for each occurrence, is independently selected from the group consisting of (C$_1$–C$_8$)alkylamino, —NR$^3$CO(CH$_2$)$_p$R$^0$, —NR$^3$CO$_2$R$^0$ and —NR$^3$SO$_2$(CH$_2$)$_p$R$^0$; R$^3$, for each occurrence, is independently H or (C$_1$–C$_6$)alkyl; R$^0$, for each occurrence, is independently (C$_1$–C$_{10}$) alkyl, phenyl or phenyl independently substituted by one to three (C$_1$–C$_4$)alkyl, (C$_1$–C$_4$)alkoxy or halo; and p is 0, 1 or 2.

This invention still more particularly provides compounds as described in the immediately preceding paragraph wherein R$^2$ is H.

This invention still more particularly provides compounds as described in the immediately preceding paragraph wherein R$^1$ is amino, —NR$^3$CO(C$_1$–C$_{10}$)alkyl, —NR$^3$CO$_2$(C$_1$–C$_8$)alkyl or —NR$^3$CO(CH$_2$)$_p$R$^0$.

This invention still more particularly provides compounds as described in the immediately preceding paragraph wherein R$^1$ is amino or —NR$^3$CO(C$_1$–C$_{10}$)alkyl).

This invention still more particularly provides toluene-4-sulfonic acid 2-(6-acetylamino-pyridin-3-yl)-2-hydroxyethyl ester. Still further, this invention provides the R enantiomer of toluene-4-sulfonic acid 2-(6-acetylamino-pyridin-3-yl)-2-hydroxyethyl ester, essentially free of its corresponding S enantiomer. Still further, this invention provides the S enantiomer of toluene-4-sulfonic acid 2-(6-acetylamino-pyridin-3-yl)-2-hydroxyethyl ester, essentially free of its corresponding R enantiomer.

This invention also provides N-(5-(2-chloro-1-hydroxyethyl)-1-pyridin-2-yl)-acetamide. Still further, this invention provides the R enantiomer of N-(5-(2-chloro-1-hydroxyethyl)-1-pyridin-2-yl)-acetamide, essentially free of its corresponding S enantiomer. Still further, this invention provides the S enantiomer of N-(5-(2-chloro-1-hydroxyethyl)-1-pyridiin-2-yl)-acetamide, essentially free of its corresponding R enantiomer.

This invention also provides compounds of the formula

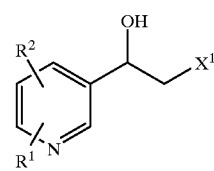

II$^A$ wherein: R$^1$ is selected from the group consisting of nitro, amino and protected amino; R$^2$ is selected from the group consisting of H, fluoro, chloro, CF$_3$, nitro, (C$_1$–C$_4$)alkyl, (C$_1$–C$_4$)alkoxy, amino and protected amino; X$^1$ is chloro or iodo; racemic mixtures thereof; R enantiomers thereof, wherein said R enantiomers are essentially free of their corresponding S enantiomers; and S enantiomers thereof, wherein said S enantiomers are essentially free of their corresponding R enantiomers thereof.

This invention particularly provides compounds as described in the immediately preceding paragraph wherein X$^1$ is chloro and said compound is an R enantiomer, essentially free of its corresponding S enantiomer. This invention also particularly provides compounds as described in the immediately preceding paragraph wherein X$^1$ is chloro and said compound is an S enantiomer, essentially free of its corresponding R enantiomer.

This invention also provides compounds of the formula

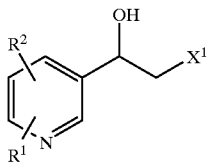

II$^A$ wherein: R$^1$ is selected from the group consisting of nitro, amino and protected amino; R$^2$ is selected from the group consisting of H, fluoro, chloro, CF$_3$, nitro, (C$_1$–C$_4$)alkyl, (C$_1$–C$_4$)alkoxy, amino and protected amino; X$^1$ is Br; and said compound is an (R) enantiomer, essentially free of its corresponding (S) enantiomer.

This invention also provides compounds of the formula

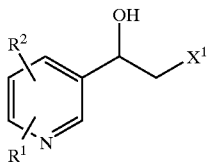

II$^A$ wherein: R$^1$ is selected from the group consisting of nitro, amino and protected amino; R$^2$ is selected from the group consisting of H, fluoro, chloro, CF$_3$, nitro, (C$_1$–C$_4$)alkyl, (C$_1$–C$_4$)alkoxy, amino and protected amino; X$^1$ is Br; and said compound is an (S) enantiomer, essentially free of its corresponding (R) enantiomer.

This invention still further provides compounds of the formula

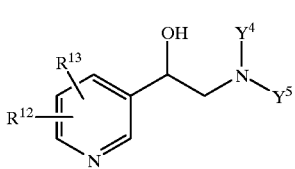

VIII wherein R$^{12}$ is selected from the group consisting of nitro and protected amino; R$^{13}$ is selected from the group consisting of H, fluoro, chloro, CF$_3$, nitro, (C$_1$–C$_4$)alkyl, (C$_1$–C$_4$)alkoxy and protected amino; Y$^4$ is an amine protecting group; and Y$^5$ is

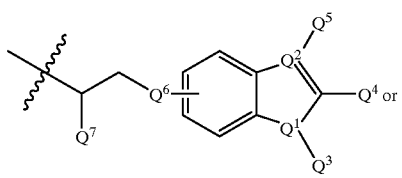

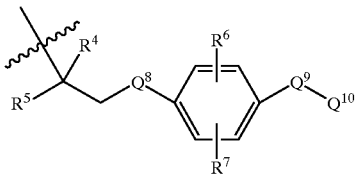

wherein Q$^1$ is oxygen, nitrogen or sulfur; Q$^2$ is carbon or nitrogen; Q$^3$ is hydrogen, —(CH$_2$)$_n$-phenyl, -(C$_1$–C$_{10}$)alkyl, —(CH$_2$)$_n$—NG$^1$G$^2$, —(CH$_2$)$_n$—CO$_2$G$^3$, —(CH$_2$)$_n$—CO—NG$^1$G$^2$, —(CH$_2$)$_n$OG$^3$, —(CH$_2$)$_n$—SO$_3$G$^3$, —(CH$_2$)$_n$—SO$_2$-(C$_1$–C$_6$)alkyl, —(CH$_2$)$_n$—SO$_2$NG$^1$G$^2$, or a heterocycle selected from the group consisting of —(CH$_2$)$_n$-pyridyl, —(CH$_2$)$_n$-pyrimidyl, —(CH$_2$)$_n$-pyrazinyl, —(CH$_2$)$_n$-isoxazolyl, —(CH$_2$)$_n$-oxazolyl, —(CH$_2$)$_n$-thiazolyl, —(CH$_2$)$_n$-(1,2,4-oxadiazolyl), —(CH$_2$)$_n$-imidazolyl, —(CH$_2$)$_n$-triazolyl and —(CH$_2$)$_n$-tetrazolyl; wherein one of the ring nitrogen atoms of said —(CH$_2$)$_n$-imidazolyl, —(CH$_2$)$_n$-triazolyl and —(CH$_2$)$_n$-tetrazolyl may optionally be substituted by (C$_1$–C$_8$)alkyl optionally independently substituted with one or more halo atoms; wherein each of said heterocycles may optionally be substituted on one or more of the ring carbon atoms by one or more substituents independently selected from the group consisting of (C$_1$–C$_8$) alkyl optionally independently substituted with one or more halo atoms, halo, nitro, cyano, —(CH$_2$)$_n$—NG$^1$G$^2$, —(CH$_2$)$_n$—CO$_2$G$^3$, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl and —(CH$_2$)$_n$—SO$_2$NG$^1$G$^2$; wherein the phenyl moiety of said —(CH$_2$)$_n$-phenyl may optionally be substituted with one or more substituents independently selected from the group consisting of (C$_1$–C$_6$)alkyl optionally independently substituted with one or more halo atoms, hydroxy, (C$_1$–C$_6$) alkoxy optionally independently substituted with one or more halo atoms, (C$_1$–C$_6$)alkylthio, fluoro, chloro, bromo, iodo, cyano, nitro, —(CH$_2$)$_n$—NG$^1$G$^2$, —(CH$_2$)$_n$—CO$_2$G$^3$, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl, —(CH$_2$)$_n$—SO$_2$NG$^1$G$^2$; —(CH$_2$)$_n$—NG$^3$—SO$_2$—G$^3$ and —(CH$_2$)$_n$—NG$^3$—SO$_2$—NG$^1$G$^2$; Q$^4$ is —(CH$_2$)$_n$—CN, —(CH$_2$)$_n$CO$_2$G$^3$, —(CH$_2$)$_n$—SO$_3$G$^3$, —(CH$_2$)$_n$—SO$_2$-(C$_1$–C$_6$)alkyl, —(CH$_2$)$_n$—SO$_2$NG$^1$G$^2$, —(CH$_2$)$_n$CH$_2$OH, —(CH$_2$)$_n$—CHO, —(CH$_2$)$_n$—CO—G$^3$, —(CH$_2$)$_n$—CONG$^1$G$^2$, or a heterocycle selected from —(CH$_2$)$_n$-thiazolyl, —(CH$_2$)$_n$-oxazolyl, —(CH$_2$)$_n$-imidazolyl, —(CH$_2$)$_n$-triazolyl, —(CH$_2$)$_n$-1,2,4-oxadiazolyl, —(CH$_2$)$_n$-isoxazolyl, —(CH$_2$)$_n$- tetrazolyl and —(CH$_2$)$_n$-pyrazolyl; wherein one of the ring nitrogen atoms of said —(CH$_2$)$_n$-imidazolyl, —(CH$_2$)$_n$-triazolyl and —(CH$_2$)$_n$-tetrazolyl may optionally be substituted by (C$_1$–C$_6$)alkyl optionally independently substituted with one or more halo atoms; wherein each of said heterocycles may optionally be substituted on one or more of the ring carbon atoms by one or more substituents independently selected from the group consisting of hydrogen, (C$_1$–C$_6$)alkyl optionally independently substituted with one or more halo atoms, —(CH$_2$)$_n$—CO—NG$^1$G$^2$, —(CH$_2$)$_n$—CO$_2$G$^3$, halo, nitro, cyano, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl, or —(CH$_2$)$_n$—SO$_2$NG$^1$G$^2$; Q$^5$ is hydrogen or (C$_1$–C$_6$)alkyl optionally independently substituted with one or more halo atoms; Q$^6$ is a covalent bond, oxygen or sulfur; Q$^7$ is hydrogen or (C$_1$–C$_6$)alkyl optionally independently substituted with one or more halo atoms; Q$^8$ and Q$^9$ are independently a covalent bond, oxygen, sulfur, NH or N-(C$_1$–C$_6$)alkyl; Q$^{10}$ is (CH$_2$)$_m$OR$^9$, (CH$_2$)$_n$CO$_2$H, (CH$_2$)$_n$COR$^{11}$, $(CH_2)_nSO_2NR^9R^{10}$, $(CH_2)_n-NR^9SO_2R^8$, $(CH_2)_nP(O)(OR^4)(OR^5)$, $(CH_2)_n-O-(CH_2)_mCO_2H$, $(CH_2)_n-O-(CH_2)_mCOR^{11}$, $(CH_2)_n-O-(CH_2)_mP(O)(OR^4)(OR^5)$, $(CH_2)_n-O-(CH_2)_mSO_2NR^9R^{10}$, or $(CH_2)_n-O-(CH_2)_m-NR^9SO_2R^8$; $R^4$ and $R^5$ are each independently hydrogen or $(C_1-C_6)$alkyl; and $R^6$ and $R^7$ are each independently hydrogen, halo, $(C_1-C_6)$alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^9SO_2R^8$, $NR^9COR^{11}$, $NR^9CO_2R^9$ or $OR^9$; where $G^1$ and $G^2$ for each occurrence are each independently hydrogen, $(C_1-C_6)$alkyl optionally independently substituted with one or more halo, $(C_1-C_6)$alkoxy$(C_1-C_6)$alkyl or $(C_3-C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur; $G^3$ for each occurrence is independently hydrogen or $(C_1-C_6)$alkyl; $R^8$ for each occurrence is independently $(C_1-C_6)$alkyl or $(C_1-C_6)$alkoxy$(C_1-C_6)$alkyl; $R^9$ and $R^{10}$ are taken separately and, for each occurrence, are independently hydrogen, $(C_1-C_6)$alkyl, $(C_3-C_8)$cycloalkyl, or $(C_1-C_6)$alkoxy$(C_1-C_6)$alkyl, or $R^9$ and $R^{10}$ are taken together with the nitrogen atom to which they are attached and form a pyrrolidine, piperidine or morpholine ring wherein said pyrrolidine, piperidine or morpholine may optionally be substituted at any carbon atom by $(C_1-C_4)$alkyl or $(C_1-C_4)$alkoxy; $R^{11}$ for each occurrence is independently hydrogen, $(C_1-C_6)$alkyl, $(C_1-C_6)$alkoxy, $NR^9R^{10}$, $(C_3-C_8)$cycloalkyl, or $(C_1-C_6)$alkoxy$(C_1-C_6)$alkyl wherein $R^9$ and $R^{10}$ are as defined above; m for each occurrence is independently an integer of 1 to 6; and n for each occurrence is independently 0 or an integer of 1 to 6; racemic mixtures thereof; R enantiomers thereof, wherein said R enantiomer is essentially free of its corresponding S enantiomer; and S enantiomers thereof, wherein said R enantiomer is essentially free of its corresponding R enantiomer; provided that: (1) when $Q^9$ is O or S then n is not 0; (2) when $Q^1$ is oxygen or sulfur then $Q^3$ is absent; and (3) when $Q^2$ is nitrogen then $Q^5$ is absent.

This invention particularly provides those compounds described in the immediately preceding paragraph wherein $Y^4$ is an amine protecting group selected from the group consisting of benzyl, $COR^{14}$, $CO_2R^{14}$ and $SO_2R^{14}$; and $R^{14}$, for each occurrence, is independently $(C_1-C_{10})$alkyl, phenyl or benzyl; wherein said phenyl and benzyl are independently optionally substituted by one to three $(C_1-C_4)$alkyl, $(C_1-C_4)$alkoxy or halo.

This invention more particularly provides those compounds described in the immediately preceding paragraph wherein $Y^5$ is

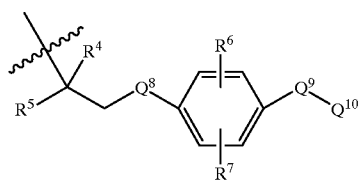

This invention still more particularly provides those compounds described in the immediately preceding paragraph wherein $R^{13}$ is H and $R^{12}$ is protected amino; said protected amino is independently selected from the group consisting of $(C_1-C_8)$alkylamino, $-NR^3CO(CH_2)_pR^0$, $-NR^3CO_2R^0$ and $-NR^3SO_2(CH_2)_pR^0$; $R^3$ is independently H or $(C_1-C_6)$alkyl; $R^0$ is independently $(C_1-C_{10})$alkyl, phenyl or phenyl independently substituted by one to three $(C_1-C_4)$alkyl, $(C_1-C_4)$alkoxy or halo; and p is 0, 1 or 2.

This invention still more particularly provides those compounds described in the immediately preceding paragraph wherein said protected amino is $NR^3CO(CH_2)_pR^0$; $R^3$ is H; $R^0$ is $CH_3$; and p is 0.

This invention still more particularly provides those compounds as described in the immediately preceding paragraph wherein $R^4$, $R^5$, $R^6$ and $R^7$ are each hydrogen; $Q^3$ is oxygen; $Q^9$ is a covalent bond; and $Q^{10}$ is $(CH_2)_mCONR^9R^{10}$.

This invention still more particularly provides those compounds as described in the immediately preceding paragraph wherein $Y^4$ is t-butyloxycarbonyl; m is 1; $R^9$ is H; and $R^{10}$ is methyl.

This invention still more particularly provides those compounds as described in the immediately preceding paragraph having the formula:

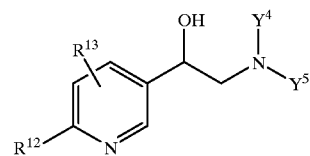

This invention still more particularly provides those compounds described in the immediately preceding paragraph which are R enantiomers.

This invention still more particularly provides N-methyl 4-(2-(2-(2-acetylaminopyridin-5-yl)-2-(R)-hydroxyethyl-N-tert-butyloxycarbonylamino)-ethoxy)-phenylacetamide.

This invention also provides a process for preparing compounds of the formula

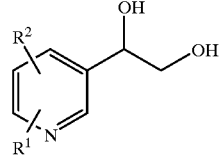

VI wherein:
$R^1$ is selected from the group consisting of nitro, amino and protected amino; and
$R^2$ is selected from the group consisting of H, fluoro, chloro, $CF_3$, nitro, $(C_1-C_4)$alkyl, $(C_1-C_4)$alkoxy, amino and protected amino comprising reacting a compound of the formula

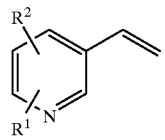

V wherein $R^1$ and $R^2$ are as defined above, with a catalyst comprising an osmium (VIII) oxide or an osmium salt and an auxiliary oxidizing agent in a reaction inert solvent.

This invention also provides a process as described in the immediately preceding paragraph additionally comprising reacting said compounds of formula (V) with said osmium (VIII) oxide or said osmium salt in the presence of a chiral auxiliary ligand and an auxiliary base.

This invention particularly provides a process of the immediately preceding paragraph wherein said chiral auxiliary ligand is $(DHQD)_2PHAL$.

This invention more particularly provides a process of the immediately preceding paragraph wherein said compound of formula (VI) has an R configuration at the 1-position of the 5-ethyl group, said compound being essentially free of its corresponding S enantiomer.

This invention still more particularly provides a process of the immediately preceding paragraph wherein $R^1$ is acetylamino and $R^2$ is H.

This invention also particularly provides a process for preparing compounds of the formula

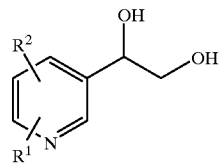

VI wherein: $R^1$ is selected from the group consisting of nitro, amino and protected amino; and $R^2$ is selected from the group consisting of H, fluoro, chloro, $CF_3$, nitro, $(C_1-C_4)$ alkyl, $(C_1-C_4)$alkoxy, amino and protected amino comprising reacting a compound of the formula

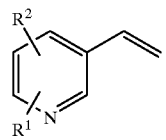

V with a catalyst comprising an osmium (VIII) oxide or an osmium salt and an auxiliary oxidizing agent in the presence of a chiral auxiliary ligand and an auxiliary base in a reaction inert solvent wherein said chiral auxiliary ligand is (DHQ)$_2$PHAL.

This invention more particularly provides a process of the immediately preceding paragraph wherein said compound of formula (VI) has an S configuration at the 1-position of the 5-ethyl group, said compound being essentially free of its corresponding R enantiomer.

This invention still more particularly provides a process of the immediately preceding paragraph wherein $R^1$ is acetylamino and $R^2$ is H.

This invention also provides a process for preparing a compound of the formula (I),

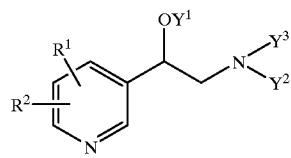

I and the racemic-enantiomeric mixtures and optical isomers of said compounds comprising:

(a) reacting a compound of the formula

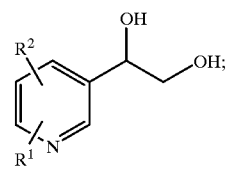

VI with an organosulfonyl chloride and a suitable base in a reaction inert solvent to form a compound of the formula

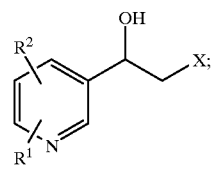

II (b) reacting said compound of formula II with a non-nucleophilic base in a reaction inert solvent to form a compound of the formula (III)

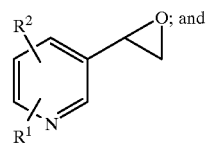

III (c) reacting said compound of formula (III) with a base and $HNY^2Y^3$ to form said compound of formula (I);

wherein:
$R^1$ is selected from the group consisting of nitro, amino and protected amino;
$R^2$ is selected from the group consisting of H, fluoro, chloro, $CF_3$, nitro, $(C_1-C_4)$alkyl, $(C_1-C_4)$alkoxy, amino and protected amino; and
Y is Br, I or trifluoromethanesulfonyloxy; and
X is organosulfonyloxy;
$Y^1$ and $Y^3$ are H;
$Y^2$ is

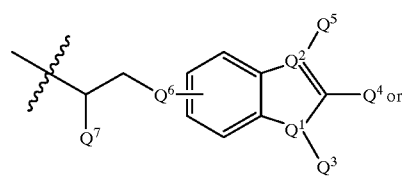

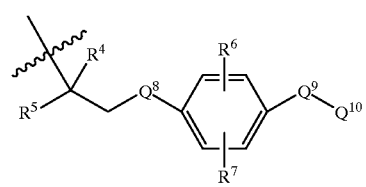

wherein:

$Q^1$ is oxygen, nitrogen or sulfur;

$Q^2$ is carbon or nitrogen;

$Q^3$ is hydrogen, —(CH$_2$)$_n$-phenyl, -(C$_1$–C$_{10}$)alkyl, —(CH$_2$)$_n$—NG$^1$G$^2$, —(CH$_2$)$_n$—CO$_2$G$^3$, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl, —(CH$_2$)$_n$—SO$_2$NG$^1$G$^2$, or a heterocycle selected from the group consisting of —(CH$_2$)$_n$-pyridyl, —(CH$_2$)$_n$-pyrimidyl, —(CH$_2$)$_n$-pyrazinyl, —(CH$_2$)$_n$-isoxazolyl, —(CH$_2$)$_n$-oxazolyl, —(CH$_2$)$_n$-thiazolyl, —(CH$_2$)$_n$-(1,2,4-oxadiazolyl), —(CH$_2$)$_n$-imidazolyl, —(CH$_2$)$_n$-triazolyl and —(CH$_2$)$_n$-tetrazolyl;

wherein one of the ring nitrogen atoms of said —(CH$_2$)$_n$-imidazolyl, —(CH$_2$)$_n$-triazolyl and —(CH$_2$)$_n$-tetrazolyl may optionally be substituted by (C$_1$–C$_8$)alkyl optionally independently substituted with one or more halo atoms; wherein each of said heterocycles may optionally be substituted on one or more of the ring carbon atoms by one or more substituents independently selected from the group consisting of (C$_1$–C$_8$)alkyl optionally independently substituted with one or more halo atoms, halo, nitro, cyano, —(CH$_2$)$_n$—NG$^1$G$^2$, —(CH$_2$)$_n$CO$_2$G$^3$, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl and —(CH$_2$)$_n$—SO$_2$NG$^1$G$^2$;

wherein the phenyl moiety of said —(CH$_2$)$_n$-phenyl may optionally be substituted with one or more substituents independently selected from the group consisting of (C$_1$–C$_6$)alkyl optionally independently substituted with one or more halo atoms, hydroxy, (C$_1$–C$_6$)alkoxy optionally independently substituted with one or more halo atoms, (C$_1$–C$_6$)alkylthio, fluoro, chloro, bromo, iodo, cyano, nitro, —(CH$_2$)$_n$—NG$^1$G$^2$, —(CH$_2$)$_n$—CO$_2$G$^3$, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl, —(CH$_2$)$_n$—SO$_2$NG$^1$G$^2$; —(CH$_2$)$_n$—NG$^3$—SO$_2$—G$^3$ and —(CH$_2$)$_n$—NG$^3$—SO$_2$—NG$^1$G$^2$;

$Q^4$ is —(CH$_2$)$_n$—CN, —(CH$_2$)$_n$CO$_2$G$^3$, —(CH$_2$)$_n$—SO$_3$G$^3$, —(CH$_2$)$_n$—SO$_2$-(C$_1$–C$_6$)alkyl, —(CH$_2$)$_n$—SO$_2$NG$^1$G$^2$, —(CH$_2$)$_n$CH$_2$OH, —(CH$_2$)$_n$—CHO, —(CH$_2$)$_n$—CO—G$^3$, —(CH$_2$)$_n$—CONG$^1$G$^2$, or a heterocycle selected from —(CH$_2$)$_n$-thiazolyl, —(CH$_2$)$_n$-oxazolyl, —(CH$_2$)$_n$-imidazolyl, —(CH$_2$)$_n$-triazolyl, —(CH$_2$)$_n$-1,2,4-oxadiazolyl, —(CH$_2$)$_n$-isoxazolyl, —(CH$_2$)$_n$-tetrazolyl and —(CH$_2$)$_n$-pyrazolyl;

wherein one of the ring nitrogen atoms of said —(CH$_2$)$_n$-imidazolyl, —(CH$_2$)$_n$-triazolyl and —(CH$_2$)$_n$-tetrazolyl may optionally be substituted by (C$_1$–C$_6$)alkyl optionally independently substituted with one or more halo atoms; wherein each of said heterocycles may optionally be substituted on one or more of the ring carbon atoms by one or more substituents independently selected from the group consisting of hydrogen, (C$_1$–C$_6$)alkyl optionally independently substituted with one or more halo atoms, —(CH$_2$)$_n$—CO—NG$^1$G$^2$, —(CH$_2$)$_n$—CO$_2$G$^3$, halo, nitro, cyano, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl, or —(CH$_2$)$_n$—SO$_2$NG$^1$G$^2$;

$Q^5$ is hydrogen or (C$_1$–C$_6$)alkyl optionally independently substituted with one or more halo atoms;

$Q^6$ is a covalent bond, oxygen or sulfur;

$Q^7$ is hydrogen or (C$_1$–C$_6$)alkyl optionally independently substituted with one or more halo atoms;

$Q^8$ and $Q^9$ are independently a covalent bond, oxygen, sulfur, NH or N-(C$_1$–C$_6$)alkyl;

$Q^{10}$ is (CH$_2$)$_m$OR$^9$, (CH$_2$)$_n$CO$_2$H, (CH$_2$)$_n$COR$^{11}$, (CH$_2$)$_n$SO$_2$NR$^9$R$^{10}$, (CH$_2$)$_n$—NR$^9$SO$_2$R$^8$, (CH$_2$)$_n$P(O)(OR$^4$)(OR$^5$), (CH$_2$)$_n$—O—(CH$_2$)$_m$CO$_2$H, (CH$_2$)$_n$—O—(CH$_2$)$_m$COR$^{11}$, (CH$_2$)$_n$—O—(CH$_2$)$_m$P(O)(OR$^4$)(OR$^5$), (CH$_2$)$_n$—O—(CH$_2$)$_m$SO$_2$NR$^9$R$^{10}$, or (CH$_2$)$_n$—O—(CH$_2$)$_m$—NR$^9$SO$_2$R$^8$;

$R^4$ and $R^5$ are each independently hydrogen or (C$_1$–C$_6$)alkyl; and $R^6$ and $R^7$ are each independently hydrogen, halo, (C$_1$–C$_6$)alkyl, nitro, cyano, trifluoromethyl, SO$_2$R$^8$, SO$_2$NR$^9$R$^{10}$, NR$^9$R$^{10}$, COR$^{11}$, CO$_2$R$^9$, (C$_1$–C$_6$)alkoxy, NR$^8$SO$_2$R$^8$, NR$^9$COR$^{11}$, NR$^9$CO$_2$R$^9$ or OR$^9$;

where $G^1$ and $G^2$ for each occurrence are each independently hydrogen, (C$_1$–C$_6$)alkyl optionally independently substituted with one or more halo, (C$_1$–C$_8$)alkoxy(C$_1$–C$_6$)alkyl or (C$_3$–C$_8$)cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or (C$_1$–C$_6$)alkyl;

$R^8$ for each occurrence is independently (C$_1$–C$_6$)alkyl or (C$_1$–C$_6$)alkoxy(C$_1$–C$_6$)alkyl;

$R^9$ and $R^{10}$ for each occurrence are independently hydrogen, (C$_1$–C$_6$)alkyl, (C$_3$–C$_8$)cycloalkyl, or (C$_1$–C$_6$)alkoxy(C$_1$–C$_6$)alkyl;

$R^{11}$ for each occurrence is independently hydrogen, (C$_1$–C$_6$)alkyl, (C$_1$–C$_6$)alkoxy, NR$^9$R$^{10}$, (C$_3$–C$_8$)cycloalkyl, or (C$_1$–C$_6$)alkoxy(C$_1$–C$_6$)alkyl wherein $R^9$ and $R^{10}$ are as defined above;

m for each occurrence is independently an integer of 1 to 6; and n for each occurrence is independently 0 or an integer of 1 to 6;

provided that:

(1) when $Q^9$ is O or S then n is not 0;

(2) when $Q^1$ is oxygen or sulfur then $Q^3$ is absent; and (3) when $Q^2$ is nitrogen then $Q^5$ is absent.

This invention still more particularly provides a process as described in the immediately preceding paragraph wherein said organosulfonyloxy is methanesulfonyloxy, benzenesulfonyloxy, poluenesulfonyloxy, p-nitrobenzenesulfonyloxy or m-nitrobenzenesulfonyloxy.

This invention also provides a process for preparing compounds of the formula

II

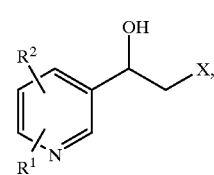

wherein: $R^1$ is selected from the group consisting of nitro, amino and protected amino; $R^2$ is selected from the group consisting of H, fluoro, chloro, CF$_3$, nitro, (C$_1$–C$_4$)alkyl, (C$_1$–C$_4$)alkoxy, amino and protected amino; and X is organosulfonyloxy, comprising: reacting a compound of the formula

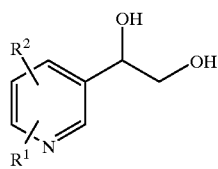

VI wherein $R^1$ and $R^2$ are as defined above, with an organosulfonyl chloride and a suitable base in a reaction inert solvent.

This invention further provides a process for preparing compounds of the formula

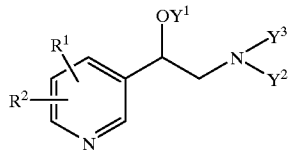

I and the racemic-enantiomeric mixtures and optical isomers of said compounds comprising:

(a) reacting a compound of the formula

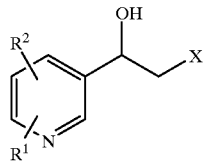

II with a non-nucleophilic base in a reaction inert solvent to form a compound of the formula (III)

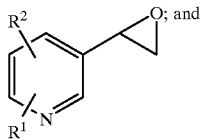

III (b) reacting said compound of formula (III) with a base and $HNY^2Y^3$ to form said compound of formula (I), wherein:

$R^1$ is selected from the group consisting of nitro, amino and protected amino;

$R^2$ is selected from the group consisting of H, fluoro, chloro, $CF_3$, nitro, $(C_1-C_4)$alkyl, $(C_1-C_4)$alkoxy, amino and protected amino;

X is an organosulfonyloxy group;

$Y^1$ and $Y^3$ are H;

$Y^2$ is

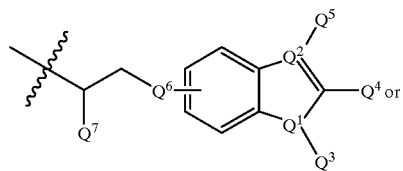

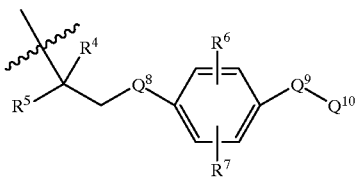

wherein:

$Q^1$ is oxygen, nitrogen or sulfur;

$Q^2$ is carbon or nitrogen;

$Q^3$ is hydrogen, $—(CH_2)_n$-phenyl, $-(C_1-C_{10})$alkyl, $—(CH_2)_nNG^1G^2$, $—(CH_2)_n—CO_2G^3$, $—(CH_2)_n—CO—NG^1G^2$, $—(CH_2)_n—OG^3$, $—(CH_2)_n—SO_3G^3$, $—(CH_2)_n—SO_2-(C_1-C_6)$alkyl, $—(CH_2)_n—SO_2NG^1G^2$, or a heterocycle selected from the group consisting of $—(CH_2)_n$-pyridyl, $—(CH_2)_n$-pyrimidyl, $—(CH_2)_n$-pyrazinyl, $—(CH_2)_n$-isoxazolyl, $—(CH_2)_n$-oxazolyl, $—(CH_2)_n$-thiazolyl, $—(CH_2)_n$-(1,2,4-oxadiazolyl), $—(CH_2)_n$-imidazolyl, $—(CH_2)_n$-triazolyl and $—(CH_2)_n$-tetrazolyl;

wherein one of the ring nitrogen atoms of said $—(CH_2)_n$-imidazolyl, $—(CH_2)_n$-triazolyl and $—(CH_2)_n$-tetrazolyl may optionally be substituted by $(C_1-C_8)$alkyl optionally independently substituted with one or more halo atoms; wherein each of said heterocycles may optionally be substituted on one or more of the ring carbon atoms by one or more substituents independently selected from the group consisting of $(C_1-C_8)$alkyl optionally independently substituted with one or more halo atoms, halo, nitro, cyano, $—(CH_2)_n—NG^1G^2$, $—(CH_2)_n—CO_2G^3$, $—(CH_2)_n—CO—NG^1G^2$, $—(CH_2)_n—OG^3$, $—(CH_2)_n—SO_3G^3$, $—(CH_2)_n—SO_2-(C_1-C_6)$alkyl and $—(CH_2)_n—SO_2NG^1G^2$;

wherein the phenyl moiety of said $—(CH_2)_n$-phenyl may optionally be substituted with one or more substituents independently selected from the group consisting of $(C_1-C_6)$alkyl optionally independently substituted with one or more halo atoms, hydroxy, $(C_1-C_6)$alkoxy optionally independently substituted with one or more halo atoms, $(C_1-C_6)$alkylthio, fluoro, chloro, bromo, iodo, cyano, nitro, $—(CH_2)_n—NG^1G^2$, $—(CH_2)_n—CO_2G^3$, $—(CH_2)_n—CO—NG^1G^2$, $—(CH_2)_n—OG^3$, $—(CH_2)_n—SO_3G^3$, $—(CH_2)_n—SO_2-(C_1-C_6)$alkyl, $—(CH_2)_n—SO_2NG^1G^2$; $—(CH_2)_n—NG^3—SO_2—G^3$ and $—(CH_2)_n—NG^3—SO_2—NG^1G^2$;

$Q^4$ is $—(CH_2)_n—CN$, $—(CH_2)_nCO_2G^3$, $—(CH_2)_n—SO_3G^3$, $—(CH_2)_n—SO_2-(C_1-C_6)$alkyl, $—(CH_2)_n—SO_2NG^1G^2$, $—(CH_2)_nCH_2OH$, $—(CH_2)_n—CHO$, $—(CH_2)_n—CO—G^3$, $—(CH_2)_n—CONG^1G^2$, or a heterocycle selected from $—(CH_2)_n$-thiazolyl, $—(CH_2)_n$-oxazolyl, $—(CH_2)_n$-imidazolyl, $—(CH_2)_n$-triazolyl, $—(CH_2)_n$-1,2,4-oxadiazolyl, $—(CH_2)_n$-isoxazolyl, $—(CH_2)_n$-tetrazolyl and $—(CH_2)_n$-pyrazolyl;

wherein one of the ring nitrogen atoms of said $—(CH_2)_n$-imidazolyl, $—(CH_2)_n$-triazolyl and $—(CH_2)_n$- tetrazolyl may optionally be substituted by $(C_1-C_6)$ alkyl optionally independently substituted with one or more halo atoms; wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, $-(CH_2)_n-CO-NG^1G^2$, $-(CH_2)_n-CO_2G^3$, halo, nitro, cyano, $-(CH_2)_n-CO-NG^1G^2$, $-(CH_2)_n-OG^3$, $-(CH_2)_n-SO_3G^3$, $-(CH_2)_n-SO_2-(C_1-C_6)$alkyl, or $-(CH_2)_n-SO_2NG^1G^2$;

$Q^5$ is hydrogen or $(C_1-C_6)$alkyl optionally independently substituted with one or more halo atoms;

$Q^6$ is a covalent bond, oxygen or sulfur;

$Q^7$ is hydrogen or $(C_1-C_6)$alkyl optionally independently substituted with one or more halo atoms;

$Q^8$ and $Q^9$ are independently a covalent bond, oxygen, sulfur, NH or N-$(C_1-C_6)$alkyl;

$Q^{10}$ is $(CH_2)_mOR^9$, $(CH_2)_nCO_2H$, $(CH_2)_nCOR^{11}$, $(CH_2)_n SO_2NR^9R^{10}$, $(CH_2)_n-NR^9SO_2R^8$, $(CH_2)_nP(O)(OR^4)(OR^5)$, $(CH_2)_n-O-(CH_2)_mCO_2H$, $(CH_2)_n-O-(CH_2)_mCOR^{11}$, $(CH_2)_n-O-(CH_2)_mP(O)(OR^4)(OR^5)$, $(CH_2)_n-O-(CH_2)_mSO_2NR^9R^{10}$, or $(CH_2)_n-O-(CH_2)_m-NR^9SO_2R^8$;

$R^4$ and $R^5$ are each independently hydrogen or $(C_1-C_6)$ alkyl; and $R^6$ and $R^7$ are each independently hydrogen, halo, $(C_1-C_6)$alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^9SO_2R^8$, $NR^9COR^{11}$, $NR^9CO_2R^9$ or $OR^9$;

where $G^1$ and $G^2$ for each occurrence are each independently hydrogen, $(C_1-C_6)$alkyl optionally independently substituted with one or more halo, $(C_1-C_8)$alkoxy$(C_1-C_6)$alkyl or $(C_3-C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or $(C_1-C_6)$alkyl;

$R^8$ for each occurrence is independently $(C_1-C_6)$alkyl or $(C_1-C_6)$alkoxy$(C_1-C_6)$alkyl;

$R^9$ and $R^{10}$ for each occurrence are independently hydrogen, $(C_1-C_6)$alkyl, $(C_3-C_8)$cycloalkyl, or $(C_1-C_6)$alkoxy$(C_1-C_6)$alkyl;

$R^{11}$ for each occurrence is independently hydrogen, $(C_1-C_6)$alkyl, $(C_1-C_6)$alkoxy, $NR^9R^{10}$, $(C_3-C_8)$ cycloalkyl, or $(C_1-C_6)$alkoxy$(C_1-C_6)$alkyl wherein $R^9$ and $R^{10}$ are as defined above;

m for each occurrence is independently an integer of 1 to 6; and n for each occurrence is independently 0 or an integer of 1 to 6;

provided that:
(1) when $Q^9$ is O or S then n is not 0;
(2) when $Q^1$ is oxygen or sulfur then $Q^3$ is absent; and
(3) when $Q^2$ is nitrogen then $Q^5$ is absent.

This invention particularly provides a process as described in the immediately preceding paragraph wherein said organosulfonyloxy is methanesulfonyloxy, benzenesulfonyloxy, p-toluenesulfonyloxy, p-nitrobenzenesulfonyloxy or m-nitrobenzenesulfonyloxy.

This invention still further provides a process for preparing compounds of the formula (I),

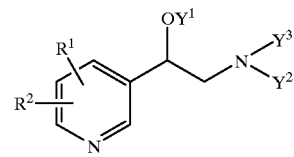

and the racemic-enantiomeric mixtures and optical isomers of said compounds comprising:

(a) reacting a compound of the formula

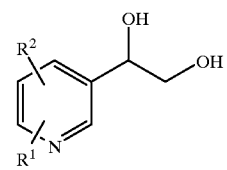

with an organosulfonyl chloride and a suitable base in a reaction inert to form a compound of the formula

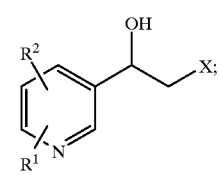

(b) reacting said compound of formula (II) with a chlorinating agent in a reaction inert solvent to form a compound of the formula (VII)

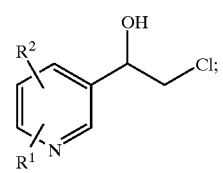

(c) reacting said compound of formula (VII) with a non-nucleophilic base in a reaction inert to form a compound of the formula (III)

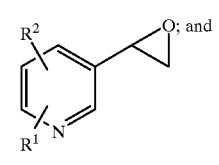

(d) reacting said compound of formula (III) with a base and $HNY^2Y^3$ to form said compound of formula (I);

wherein:

$R^1$ is selected from the group consisting of nitro, amino and protected amino;

$R^2$ is selected from the group consisting of H, fluoro, chloro, $CF_3$, nitro, $(C_1-C_4)$alkyl, $(C_1-C_4)$alkoxy, amino and protected amino; and X is organosulfonyloxy;
$Y^1$ and $Y^3$ are H;
$Y^2$ is

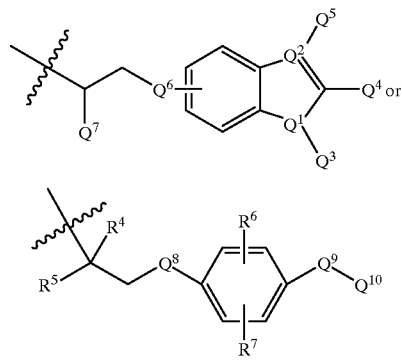

wherein:
$Q^1$ is oxygen, nitrogen or sulfur;
$Q^2$ is carbon or nitrogen;
$Q^3$ is hydrogen, $—(CH_2)_n$-phenyl, -$(C_1–C_{10})$alkyl, $—(CH_2)_n—NG^1G^2$, $—(CH_2)_n—CO_2G^3$, $—(CH_2)_n—CO—NG^1G^2$, $—(CH_2)_n—OG^3$, $—(CH_2)_n—SO_3G^3$, $—(CH_2)_n—SO_2-(C_1–C_6)$alkyl, $—(CH_2)_n—SO_2NG^1G^2$, or a heterocycle selected from the group consisting of $—(CH_2)_n$-pyridyl, $—(CH_2)_n$-pyrimidyl, $—(CH_2)_n$-pyrazinyl, $—(CH_2)_n$-isoxazolyl, $—(CH_2)_n$-oxazolyl, $—(CH_2)_n$-thiazolyl, $—(CH_2)_n$-(1,2,4-oxadiazolyl), $—(CH_2)_n$-imidazolyl, $—(CH_2)_n$-triazolyl and $—(CH_2)_n$-tetrazolyl;
  wherein one of the ring nitrogen atoms of said $—(CH_2)_n$-imidazolyl, $—(CH_2)_n$-triazolyl and $—(CH_2)_n$-tetrazolyl may optionally be substituted by $(C_1–C_8)$alkyl optionally independently substituted with one or more halo atoms; wherein each of said heterocycles may optionally be substituted on one or more of the ring carbon atoms by one or more substituents independently selected from the group consisting of $(C_1–C_8)$alkyl optionally independently substituted with one or more halo atoms, halo, nitro, cyano, $—(CH_2)_n—NG^1G^2$, $—(CH_2)_n—CO_2G^3$, $—(CH_2)_n—CO—NG^1G^2$, $—(CH_2)_n—OG^3$, $—(CH_2)_n—SO_3G^3$, $—(CH_2)_n—SO_2-(C_1–C_6)$alkyl and $—(CH_2)_n—SO_2NG^1G^2$;
  wherein the phenyl moiety of said $—(CH_2)_n$-phenyl may optionally be substituted with one or more substituents independently selected from the group consisting of $(C_1–C_6)$alkyl optionally independently substituted with one or more halo atoms, hydroxy, $(C_1–C_6)$alkoxy optionally independently substituted with one or more halo atoms, $(C_1–C_6)$alkylthio, fluoro, chloro, bromo, iodo, cyano, nitro, $—(CH_2)_n—NG^1G^2$, $—(CH_2)_n—CO_2G^3$, $—(CH_2)_n—CO—NG^1G^2$, $—(CH_2)_n—OG^3$, $—(CH_2)_n—SO_3G^3$, $—(CH_2)_n—SO_2-(C_1–C_6)$alkyl, $—(CH_2)_n—SO_2NG^1G^2$; $—(CH_2)_n—NG^3—SO_2—G^3$ and $—(CH_2)_n—NG^3—SO_2—NG^1G^2$;
$Q^4$ is $—(CH_2)_n—CN$, $—(CH_2)_nCO_2G^3$, $—(CH_2)_n—SO_3G^3$, $—(CH_2)_n—SO_2-(C_1–C_6)$alkyl, $—(CH_2)_n—SO_2NG^1G^2$, $—(CH_2)_nCH_2OH$, $—(CH_2)_n—CHO$, $—(CH_2)_n—CO—G^3$, $—(CH_2)_n—CONG^1G^2$, or a heterocycle selected from $—(CH_2)_n$-thiazolyl, $—(CH_2)_n$-oxazolyl, $—(CH_2)_n$-imidazolyl, $—(CH_2)_n$-triazolyl, $—(CH_2)_n$-1,2,4-oxadiazolyl, $—(CH_2)_n$-isoxazolyl, $—(CH_2)_n$-tetrazolyl and $—(CH_2)_n$-pyrazolyl;
  wherein one of the ring nitrogen atoms of said $—(CH_2)_n$-imidazolyl, $—(CH_2)_n$-triazolyl and $—(CH_2)_n$-tetrazolyl may optionally be substituted by $(C_1–C_6)$alkyl optionally independently substituted with one or more halo atoms; wherein each of said heterocycles may optionally be substituted on one or more of the ring carbon atoms by one or more substituents independently selected from the group consisting of hydrogen, $(C_1–C_6)$alkyl optionally independently substituted with one or more halo atoms, $—(CH_2)_n—CO—NG^1G^2$, $—(CH_2)_n—CO_2G^3$, halo, nitro, cyano, $—(CH_2)_n—CO—NG^1G^2$, $—(CH_2)_n—OG^3$, $—(CH_2)_n—SO_3G^3$, $—(CH_2)_n—SO_2-(C_1–C_6)$alkyl, or $—(CH_2)_n—SO_2NG^1G^2$;
$Q^5$ is hydrogen or $(C_1–C_6)$alkyl optionally independently substituted with one or more halo atoms;
$Q^6$ is a covalent bond, oxygen or sulfur;
$Q^7$ is hydrogen or $(C_1–C_6)$alkyl optionally independently substituted with one or more halo atoms;
$Q^8$ and $Q^9$ are independently a covalent bond, oxygen, sulfur, NH or N-$(C_1–C_6)$alkyl;
$Q^{10}$ is $(CH_2)_mOR^9$, $(CH_2)_nCO_2H$, $(CH_2)_nCOR^{11}$, $(CH_2)_nSO_2NR^9R^{10}$, $(CH_2)_n—R^9SO_2R^8$, $(CH_2)_nP(O)(OR^4)(OR^5)$, $(CH_2)_n—O—(CH_2)_mCO_2H$, $(CH_2)_n—O—(CH_2)_mCOR^{11}$, $(CH_2)_n—O—(CH_2)_mP(O)(OR^4)(OR^5)$, $(CH_2)_n—O—(CH_2)_mSO_2NR^9R^{10}$, or $(CH_2)_n—O—(CH_2)_m—NR^9SO_2R^9$;
$R^4$ and $R^5$ are each independently hydrogen or $(C_1–C_6)$ alkyl; and
$R^6$ and $R^7$ are each independently hydrogen, halo, $(C_1–C_6)$alkyl, nitro, cyano, trifluoromethyl, $SO_2R^8$, $SO_2NR^9R^{10}$, $NR^9R^{10}$, $COR^{11}$, $CO_2R^9$, $(C_1–C_6)$alkoxy, $NR^9SO_2R^8$, $NR^9COR^{11}$, $NR^9CO_2R^9$ or $OR^9$;
  where $G^1$ and $G^2$ for each occurrence are each independently hydrogen, $(C_1–C_8)$alkyl optionally independently substituted with one or more halo, $(C_1–C_8)$alkoxy$(C_1–C_6)$alkyl or $(C_3–C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;
  $G^3$ for each occurrence is independently hydrogen or $(C_1–C_6)$alkyl;
  $R^8$ for each occurrence is independently $(C_1–C_6)$alkyl or $(C_1–C_6)$alkoxy$(C_1–C_6)$alkyl;
  $R^9$ and $R^{10}$ for each occurrence are independently hydrogen, $(C_1–C_6)$alkyl, $(C_3–C_8)$cycloalkyl, or $(C_1–C_6)$alkoxy$(C_1–C_6)$alkyl;
  $R^{11}$ for each occurrence is independently hydrogen, $(C_1–C_6)$alkyl, $(C_1–C_6)$alkoxy, $NR^9R^{10}$, $(C_3–C_8)$cycloalkyl, or $(C_1–C_6)$alkoxy$(C_1–C_6)$alkyl wherein $R^9$ and $R^{10}$ are as defined above;
  m for each occurrence is independently an integer of 1 to 6; and
  n for each occurrence is independently 0 or an integer of 1 to 6;
provided that:
  (1) when $Q^9$ is O or S then n is not 0;
  (2) when $Q^1$ is oxygen or sulfur then $Q^3$ is absent; and
  (3) when $Q^2$ is nitrogen then $Q^5$ is absent.
  This invention particularly provides a process as described in the immediately preceding paragraph wherein said chlorinating agent is lithium chloride and said organosulfonyloxy is selected from the group selected consisting of methanesulfonyloxy, benzenesulfonyloxy, p-toluenesulfonyloxy, p-nitrobenzenesulfonyloxy or m-nitrobenzenesulfonyloxy.

This invention still further provides a process for preparing compounds of the formula

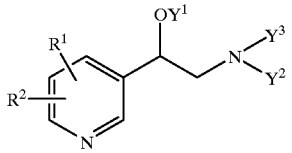

I and the racemic-enantiomeric mixtures and optical isomers of said compounds comprising:

(a) reacting a compound of the formula

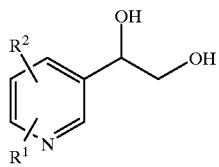

VI with an organosulfonyl chloride and a suitable base in a reaction inert solvent to form a compound of the formula (II),

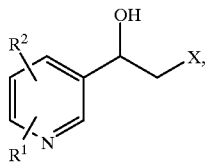

II (b) reacting said compound of formula (II) with a non-nucleophilic base in a reaction inert solvent to form a compound of the formula (III)

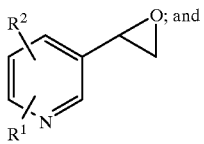

III and (c) reacting said compound of formula (III) with a base and $HNY^2Y^3$ to form said compound of formula (I), wherein:

$R^1$ is selected from the group consisting of nitro, amino and protected amino;

$R^2$ is selected from the group consisting of H, fluoro, chloro, $CF_3$, nitro, $(C_1-C_4)$alkyl, $(C_1-C_4)$alkoxy, amino and protected amino;

X is an organosulfonyloxy group;

$Y^1$ and $Y^3$ are H;

$Y^2$ is

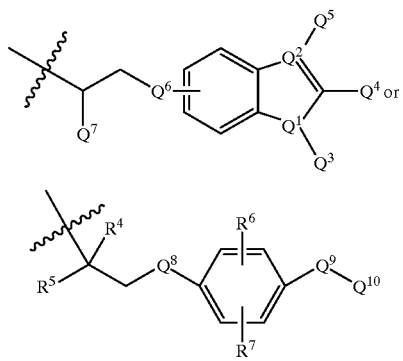

wherein:

$Q^1$ is oxygen, nitrogen or sulfur;

$Q^2$ is carbon or nitrogen;

$Q^3$ is hydrogen, —$(CH_2)_n$-phenyl, -$(C_1-C_{10})$alkyl, —$(CH_2)_n$—$NG^1G^2$, —$(CH_2)_n$—$CO_2G^3$, —$(CH_2)_n$—CO—$NG^1G^2$, —$(CH_2)_n$—$OG^3$, —$(CH_2)_n$—$SO_3G^3$, —$(CH_2)_n$—$SO_2$-$(C_1-C_6)$alkyl, —$(CH_2)_n$—$SO_2NG^1G^2$, or a heterocycle selected from the group consisting of —$(CH_2)_n$-pyridyl, —$(CH_2)_n$-pyrimidyl, —$(CH_2)_n$-pyrazinyl, —$(CH_2)_n$-isoxazolyl, —$(CH_2)_n$-oxazolyl, —$(CH_2)_n$-thiazolyl, —$(CH_2)_n$-(1,2,4-oxadiazolyl), —$(CH_2)_n$-imidazolyl, —$(CH_2)_n$-triazolyl and —$(CH_2)_n$-tetrazolyl;

wherein one of the ring nitrogen atoms of said —$(CH_2)_n$- imidazolyl, —$(CH_2)_n$-triazolyl and —$(CH_2)_n$-tetrazolyl may optionally be substituted by $(C_1-C_8)$ alkyl optionally independently substituted with one or more halo atoms; wherein each of said heterocycles may optionally be substituted on one or more of the ring carbon atoms by one or more substituents independently selected from the group consisting of $(C_1-C_8)$alkyl optionally independently substituted with one or more halo atoms, halo, nitro, cyano, —$(CH_2)_n$—$NG^1G^2$, —$(CH_2)_n$—$CO_2G^3$, —$(CH_2)_n$—CO—$NG^1G^2$, —$(CH_2)_n$—$OG^3$, —$(CH_2)_n$—$SO_3G^3$, —$(CH_2)_n$—$SO_2$-$(C_1-C_6)$alkyl and —$(CH_2)_n$—$SO_2NG^1G^2$;

wherein the phenyl moiety of said —$(CH_2)_n$-phenyl may optionally be substituted with one or more substituents independently selected from the group consisting of $(C_1-C_6)$alkyl optionally independently substituted with one or more halo atoms, hydroxy, $(C_1-C_6)$alkoxy optionally independently substituted with one or more halo atoms, $(C_1-C_6)$alkylthio, fluoro, chloro, bromo, iodo, cyano, nitro, —$(CH_2)_n$—$NG^1G^2$, —$(CH_2)_n$—$CO_2G^3$, —$(CH_2)_n$—CO—$NG^1G^2$, —$(CH_2)_n$—$OG^3$, —$(CH_2)_n$$SO_3G^3$, —$(CH_2)_n$—$SO_2$-$(C_1-C_6)$alkyl, —$(CH_2)_n$—$SO_2NG^1G^2$; —$(CH_2)_n$—$NG^3$—$SO_2$—$G^3$ and —$(CH_2)_n$—$NG^3$—$SO_2$—$NG^1G^2$;

$Q^4$ is —$(CH_2)_n$—CN, —$(CH_2)_nCO_2G^3$, —$(CH_2)_n$—$SO_3G^3$, —$(CH_2)_n$—$SO_2$-$(C_1-C_6)$alkyl, —$(CH_2)_n$—$SO_2NG^1G^2$, —$(CH_2)_nCH_2OH$, —$(CH_2)_n$—CHO, —$(CH_2)_n$—CO—$G^3$, —$(CH_2)_n$—$CONG^1G^2$, or a heterocycle selected from —$(CH_2)_n$-thiazolyl, —$(CH_2)_n$-oxazolyl, —$(CH_2)_n$-imidazolyl, —$(CH_2)_n$-triazolyl, —$(CH_2)_n$-1,2,4-oxadiazolyl, —$(CH_2)_n$-isoxazolyl, —$(CH_2)_n$-tetrazolyl and —$(CH_2)_n$-pyrazolyl;

wherein one of the ring nitrogen atoms of said —$(CH_2)_n$- imidazolyl, —$(CH_2)_n$-triazolyl and —$(CH_2)_n$- tetrazolyl may optionally be substituted by $(C_1-C_6)$ alkyl optionally independently substituted with one or more halo atoms; wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, $-(CH_2)_n-CO-NG^1G^2$, $-(CH_2)_n-CO_2G^3$, halo, nitro, cyano, $-(CH_2)_n-CO-NG^1G^2$, $-(CH_2)_n-OG^3$, $-(CH_2)_n-SO_3G^3$, $-(CH_2)_n-SO_2-(C_1-C_6)$alkyl, or $-(CH_2)_n-SO_2NG^1G^2$;

$Q^5$ is hydrogen or $(C_1-C_6)$alkyl optionally independently substituted with one or more halo atoms;

$Q^6$ is a covalent bond, oxygen or sulfur;

$Q^7$ is hydrogen or $(C_1-C_6)$alkyl optionally independently substituted with one or more halo atoms;

$Q^8$ and $Q^9$ are independently a covalent bond, oxygen, sulfur, NH or N-$(C_1-C_6)$alkyl;

$Q^{10}$ is $(CH_2)_mOR^9$, $(CH_2)_nCO_2H$, $(CH_2)_nCOR^{11}$, $(CH_2)_n SO_2NR^9R^{10}$, $(CH_2)_n-NR^9SO_2R^8$, $(CH_2)_nP(O)(OR^4)(OR^5)$, $(CH_2)_n-O-(CH_2)_mCO_2H$, $(CH_2)_n-O-(CH_2)_mCOR^{11}$, $(CH_2)_n-O-(CH_2)_mP(O)(OR^4)(OR^5)$, $(CH_2)_n-O-(CH_2)_mSO_2NR^9R^{10}$, or $(CH_2)_n-O-(CH_2)_m-NR^9SO_2R^8$;

$R^4$ and $R^5$ are each independently hydrogen or $(C_1-C_6)$ alkyl; and $R^6$ and $R^7$ are each independently hydrogen, halo, $(C_1-C_6)$alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^9SO_2R^8$, $NR^9COR^{11}$, $NR^9CO_2R^9$ or $OR^9$;

where $G^1$ and $G^2$ for each occurrence are each independently hydrogen, $(C_1-C_6)$alkyl optionally independently substituted with one or more halo, $(C_1-C_8)$alkoxy$(C_1-C_6)$alkyl or $(C_3-C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or $(C_1-C_6)$alkyl;

$R^8$ for each occurrence is independently $(C_1-C_6)$alkyl or $(C_1-C_6)$alkoxy$(C_1-C_6)$alkyl;

$R^9$ and $R^{10}$ for each occurrence are independently hydrogen, $(C_1-C_6)$alkyl, $(C_3-C_8)$cycloalkyl, or $(C_1-C_6)$alkoxy$(C_1-C_6)$alkyl;

$R^{11}$ for each occurrence is independently hydrogen, $(C_1-C_6)$alkyl, $(C_1-C_6)$alkoxy, $NR^9R^{10}$, $(C_3-C_8)$ cycloalkyl, or $(C_1-C_6)$alkoxy$(C_1-C_6)$alkyl wherein $R^9$ and $R^{10}$ are as defined above;

m for each occurrence is independently an integer of 1 to 6; and n for each occurrence is independently 0 or an integer of 1 to 6;

provided that:

(1) when $Q^9$ is O or S then n is not 0;

(2) when $Q^1$ is oxygen or sulfur then $Q^3$ is absent; and (3) when $Q^2$ is nitrogen then $Q^5$ is absent.

This invention particularly provides a process as described in the immediately preceding paragraph wherein said organosulfonyloxy is methanesulfonyloxy, benzenesulfonyloxy, p-toluenesulfonyloxy, p-nitrobenzenesulfonyloxy or m-nitrobenzenesulfonyloxy.

This invention also provides a process for preparing a compound of the formula (XIII)

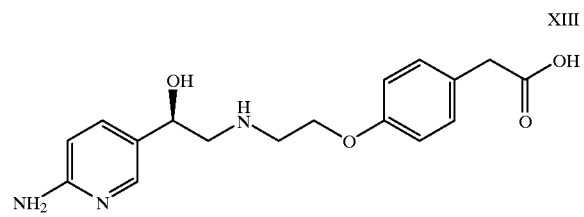

comprising reacting a compound of the formula (XIV)

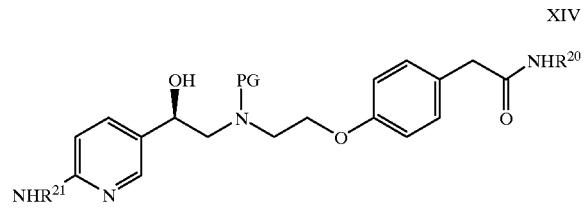

wherein:

PG is an amine protecting group; $R^{20}$ is $(C_1-C_8)$alkyl; $R^{21}$ is selected from the group consisting of $(C_1-C_8)$alkyl, $COR^{22}$, $CO_2R^{22}$ and $SO_2R^{22}$; and $R^{22}$ is $(C_1-C_8)$alkyl with an aqueous acid to form said compound of formula XIII.

This invention particularly provides a process as described in the immediately preceding paragraph wherein said amine protecting group is selected from the group consisting of $COR^{22}$, $CO_2R^{22}$ and $SO_2R^{22}$; and $R^{22}$ is $(C_1-C_8)$alkyl, This invention more particularly provides a process as described in the immediately preceding paragraph wherein said compound of formula XIV is N-methyl 4-(2-(2-(2-acetylaminopyridin-5-yl)-2-(R)-hydroxyethyl-N-tert-butyloxycarbonylamino)-ethoxy)-phenylacetamide.

This invention also provides a process for preparing a compound of the formula

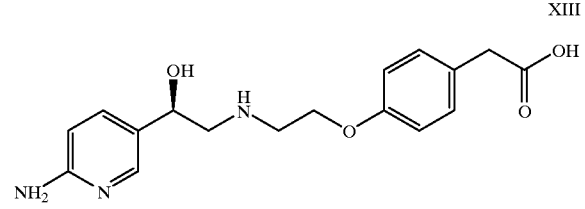

comprising:

(a) reacting a compound of the formula

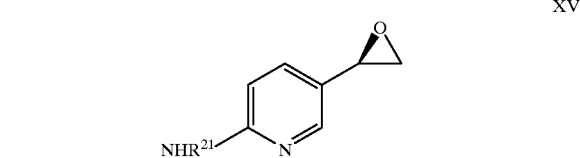

wherein $R^{21}$ is $COR^{22}$ and $R^{22}$ is $(C_1-C_8)$alkyl with a compound of the formula

XVI

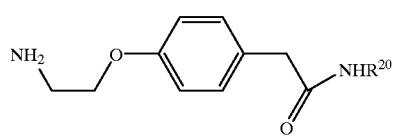

wherein $R^{20}$ is $(C_1-C_8)$alkyl in a reaction inert solvent to form a compound of the formula

XVII

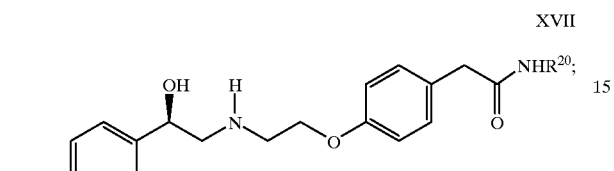

(b) reacting said compound of formula (XVII) with an acid anhydride, a dicarbonate or an acid chloride to form a compound of the formula

XIV

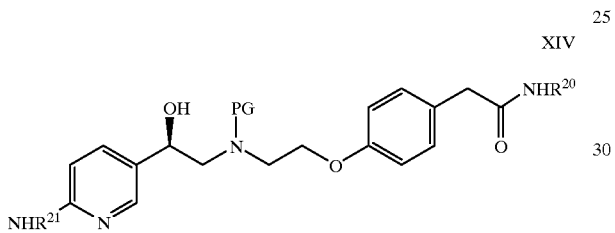

wherein $R^{20}$ and $R^{21}$ are as defined above and PG is an amine protecting group; and (c) reacting said compound of formula (XIV) with an aqueous acid to form said compound of formula (XIII).

This invention particularly provides a process as described in the immediately preceding paragraph wherein said amine protecting group is selected from the group consisting of $COR^{22}$ and $CO_2R^{22}$; and $R^{22}$ is $(C_1-C_8)$alkyl.

This invention more particularly provides a process as described in the immediately preceding paragraph wherein said compound of formula (XVII) is reacted with a dicarbonate.

This invention still more particularly provides a process as described in the immediately preceding paragraph wherein $R^{21}$ is acetyl, $R^{20}$ is methyl and PG is tert-butyloxycarbonyl.

This invention is also particularly directed to any of the processes recited hereinabove wherein said compounds of formulae (II), (III) or (VI) have the (R) configuration, said compounds being essentially free of their (S) enantiomer. This invention is also particularly directed to any of the processes recited hereinabove wherein said compounds of formulae (II), (III) or (VI) have the (S) configuration, said compounds being essentially free of their (R) enantiomer.

DETAILED DESCRIPTION OF THE INVENTION

A process for the manufacture of a compound of formula (I) as defined above is provided as a feature of the invention and is illustrated by the following procedure, set forth in Scheme I, in which the meanings of generic radicals are as described hereinbelow unless otherwise specified.

Scheme 1

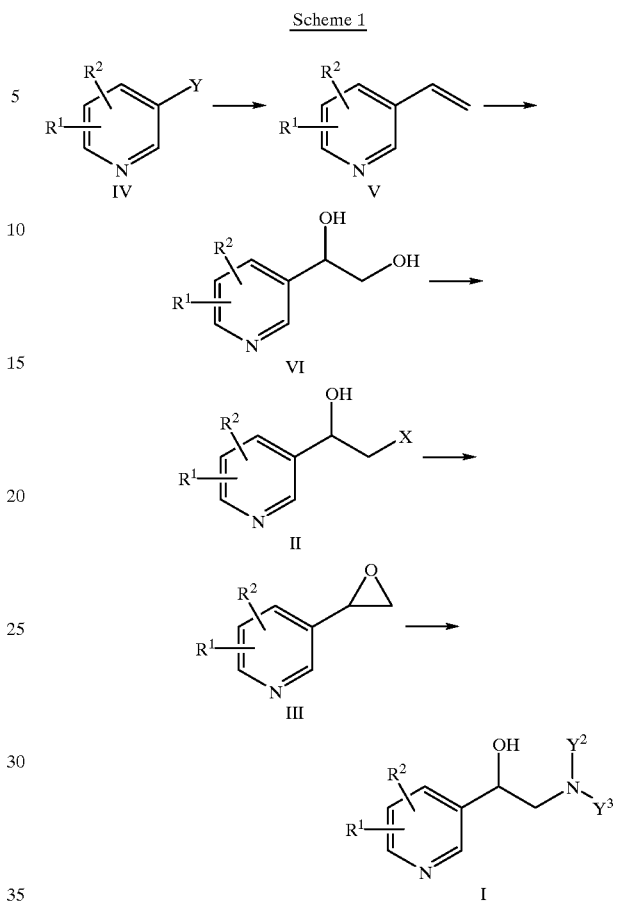

Processes for the manufacture of a compound of formula (III) as defined above are illustrated by the following procedures.

The compounds of formula (I) can be synthesized from compounds of formula (III) by reaction with an amine of formula $HNY^2Y^3$, with $H_2NY^2$ being the preferred amine. This reaction is typically carried out by reacting an amine of formula $HNY^2Y^3$ with an epoxide of formula (III) in a polar aprotic solvent such as dimethyl sulfoxide, dimethyl formamide, acetonitriie or a lower alkanol such as ethanol, 2-propanol or butanol at a temperature from about $-10°$ C. to about $125°$ C. Preferably the solvent is dimethyl sulfoxide and the reaction is carried out at a temperature from about $0°$ C. to about $10°$ C. If compound (III) was prepared in a stereospecific manner, as when a chiral auxiliary ligand is utilized in the step preparing the compound of formula (VI), the optical purity of the product, compound (I) will be preserved.

Alternatively, to prepare the compounds of formula (I) when $Y^2$ is H, the amine of formula $H_2NY^3$ can be pretreated with a suitable amine protecting group. It is preferred to react said amine with N-(trimethylsilyl)acetamide to form a silylated compound of the formula $(CH_3)_3SiNHY^3$. This prevents the secondary amine which results as a product of the reaction from reacting with a second epoxide molecule. This reaction is typically carried out in a polar aprotic solvent such as dimethyl sulfoxide, dimethyl formamide, acetonitrile or a lower alkanol such as ethanol, 2-propanol or butanol at a temperature from about $-10°$ C. to about $125°$ C. Preferably, the silylation is carried out at about $25°$ C. and the reaction with the epoxide is carried out at about $60°$ C.

After silylation is complete, the compound of formula (CH$_3$)$_3$SiNHY$^3$ is reacted with the epoxide of formula (III) as described above.

It is often desirable, when performing the coupling reaction of the epoxide of formula (III) with the amine of the formula H$_2$NY$^3$, to react the coupled product of the formula (XI)

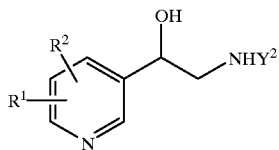

XI with an organic acid anhydride, a dicarbonate or an organic acid chloride to form a compound of the formula (XII)

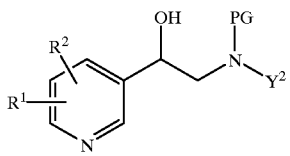

XII wherein R$^1$, R$^2$ and Y$^2$ are as defined herein and PG is an amine protecting group. The term "amine protecting group" includes an organic radical which is readily attached to an amine nitrogen atom and which block said nitrogen atom from reacting with reagents and substrates used in and intermediates and transition state molecules formed in subsequent chemical transformations. Said organic radical is readily removable under mild conditions. Where used herein, the phrase "mild conditions" defines conditions which are capable of removing a protecting group but which do not have any effect upon any other portions of the substrate to which said protecting group is attached. The compounds of formula (XII) are converted, by reaction with aqueous acid, to compounds of formula (I) wherein R$^1$ is nitro or amino; R$^2$ is H, fluoro, chloro, CF$_3$, nitro, (C$_1$–C$_4$) alkyl, (C$_1$–C$_4$)alkoxy and amino; and Y$^2$ is as defined above wherein all amine and carboxyl radicals contained within Y$^2$ are free base and free acid forms of said amine and carboxyl radicals. Said reaction with aqueous acid is carried out with an aqueous acid such as sulfuric acid, hydrochloric acid and the like at a temperature of about 25° C. to about 100° C. for one hour to forty-eight hours. Preferably, the aqueous acid is hydrochloric acid and the reaction temperature is maintained at about 90° C. to about 100° C. for about twenty-four hours.

The compounds of formula (III) may be prepared by treating a compound of formula (II) with a non-nucleophilic base. Generally, it is preferred that the non-nucleophilic base be selected from the group consisting of sodium hydroxide, potassium hydroxide, sodium hydride, potassium tert-butoxide or 1,8-diazabicyclo[5.4.0]undec-7-ene. The reaction is preferably conducted by stirring the substrate compound of formula (II) together with the appropriate non-nucleophilic base in a reaction inert solvent at a temperature of about –20° C. to about 100° C. Where used herein, the term reaction inert solvent refers to any solvent which does not interact with starting materials, reagents, intermediates or products in a manner which adversely affects the reaction or the yield of the desired product. Further, the term reaction inert solvent may refer to a single, dual or multiple solvent system depending upon the nature of the reaction and the solubility of the substrate and/or reagents being disclosed. With respect to this particular reaction, it is preferred that the solvent is a polar, non-hydroxylic solvent such as an ether derivative including but not limited to tetrahydrofuran, dioxane and dimethoxyethane; chlorinated hydrocarbons including but not limited to carbon tetrachloride, chloroform and methylene chloride; aromatic hydrocarbons including but not limited to benzene, toluene and xylene; dimethylformamide; dimethylsulfoxide or any mixture of these solvents. Generally the most preferred solvent is tetrahydrofuran.

When the compounds of formula (II) disclosed herein are organosulfonyloxy derivatives, said compounds may be prepared by reacting an appropriate compound of formula (VI) with an organosulfonyl chloride in the presence of a suitable base. Suitable bases which may be used to effect this transformation include the lower trialkylamines, pyridine and pyridine derivatives. Preferred bases within those groups include but are not limited to triethylamine, diisopropylethylamine, 2,4,6-collidine and 2,6-lutidine. Pyridine is the most preferred base. Suitable organosulfonyi chlorides include methanesulfonyl chloride, p-nitrobenzenesulfonyl chloride, m-nitrobenzenesulfonyl chloride, p-toluenesulfonyl chloride and benzenesulfonyl chloride. A generally preferred organosulfonyl chloride derivative is p-toluenesulfonyl chloride. The reaction is conveniently conducted by stirring the desired substrate compound of formula (VI) together with the appropriate organosulfonyl chloride in a reaction inert solvent at a temperature of about –20° C. to about 50° C. It is preferred that the solvent is a polar solvent such as an ether derivative including but not limited to tetrahydrofuran, dioxane and dimethoxyethane; chlorinated hydrocarbons including but not limited to carbon tetrachloride, chloroform and methylene chloride; aromatic hydrocarbons including but not limited to benzene, toluene and xylene; dimethylformamide; N-methyl-2-pyrrolidinone; dimethylacetamide; pyridine or any mixture of these solvents. Generally the most preferred solvent is pyridine. Due to the presence of chloride ion in this reaction, the reaction product may be contaminated with 2-chloro derivatives. These mixtures can be converted entirely to the 2-chloro derivatives as described below.

To prepare the compounds of formula (II$^A$) wherein X$^1$ is halo, the 2-organosulfonyloxy derivatives of the compound of formula (II) or mixtures thereof containing 2-chloro derivatives of the formula (II$^A$) with a halogenating agent in a reaction inert solvent. The reaction may be conducted conveniently at a temperature of from about 25° C. to the reflux temperature of the solvent utilized. It is generally preferred to conduct the reaction at the reflux temperature. Halogenating agents are compounds which are capable of transferring a halo group to an organic substrate, said substrate having a leaving group which can be displaced by said halide ion. Preferred halogenating agents are lithium halides. A particularly preferred chlorinating agent used to prepare the compounds of formula (VII) is lithium chloride. A preferred solvent is ethanol, The compounds of formula (VI) disclosed herein may be prepared by reacting an appropriate compound of formula (V) with a catalyst comprised of osmium (VIII) oxide or an osmium salt, in the presence of an auxiliary oxidizing agent, and optionally in the presence of a chiral auxiliary ligand such as (DHQD)$_2$PHAL or (DHQD)$_2$PYR and an auxiliary base. When it is desirable to use a catalyst other than osmium (VIII) oxide in this reaction, the catalyst is generally selected from osmium metal, potassium osmate (VI) dihydrate and osmium (III) chloride. Generally, it is preferred to use osmium tetroxide as the catalyst when conducting this reaction. Auxiliary oxidizing agents that may be employed include but are not limited to potassium ferricyanide, sodium ferricyanide, potassium persulfate, sodium persulfate, potassium chlorate, sodium chlorate and N-methylmorpholine-N-oxide (the latter oxidizing agent may only be used in the absence of chiral auxiliary ligands such as (DHQD)$_2$PHAL or (DHQD)$_2$PYR). It may also be desirable to use a mixture of auxiliary oxidizing agents to achieve optimum performance in this reaction. An especially suitable mixture of auxiliary oxidizing agents is sodium persulfate and potassium ferricyanide. Chiral auxiliary ligands that may be used, in addition to those already recited, include hydroquinidine indolinediyl diether ((DHQD)IND), hydroquinine phthalazinediyl diether ((DHQ)$_2$PHAL), hydroquinine pyrimindinediyl diether ((DHQ)$_2$PYR), hydroquinine indolinediyl diether ((DHQ)IND), hydroquinidine phenanthrinediyl diether (DHQD-PHN) and hydroquinine phenanthrinediyl diether (DHQ-PHN). The reaction is typically conducted by stirring the desired substrate compound of formula (V) together with the appropriate reagents recited above in a polar solvent at a temperature of about –10° C. to about 70° C. The reaction is conveniently conducted at about 20° C. Polar solvents which are generally useful in this reaction include water, a lower alkanol, an ether or a mixture of any of these solvents. A lower alkanol is an alcohol containing from one to four carbon atoms.

The dihydroxylation reaction disclosed in the preceding paragraph may be conducted either in the presence or in the absence of a chiral auxiliary ligand. When the reaction is conducted in the absence of a chiral auxiliary ligand, the diol product is racemic. When the reaction is conducted in the presence of a chiral auxiliary ligand, the dihydroxylation reaction proceeds stereoselectively, resulting in an essentially optically pure diol product.

The compounds of formula (V) disclosed herein may be prepared by reacting a compound of formula (IV) with ethylene gas in the presence of a base, a phosphine derivative and a palladium catalyst. Suitable bases for the reaction include lower trialkylamines, sodium carbonate, potassium carbonate, sodium bicarbonate and potassium bicarbonate. Generally, triethylamine is preferred. Suitable phosphine derivatives include triarylphosphines such as triphenylphosphine, diphenyl-2-pyridylphosphine and tri-ortho-tolylphosphine, with the latter being generally preferred. When Y is iodo, the palladium catalyst may be selected from a variety of palladium salts and complexes such as but not limited to palladium metal on carbon or some other suitable solid support, allylpalladium chloride dimer, palladium (II) chloride, palladium (II) acetate, palladium (0) tetrakis(triphenylphosphine), palladium (II) bis (triphenylphosphine) chloride, palladium (0) bis (dibenzylideneacetone) and palladium (0) bis(benzonitrile). When Y is bromo or trifluoromethanesulfonyloxy, the palladium catalyst may be selected from a variety of palladium salts and complexes such as but not limited to allylpalladium chloride dimer, palladium (II) chloride, palladium (II) acetate, palladium (0) tetrakis(triphenylphosphine), palladium (II) bis(triphenylphosphine) chloride, palladium (0) bis(dibenzylideneacetone), palladium (0) bis(benzonitrile) and allylpalladium chloride dimer. Palladium (II) acetate is especially preferred. The reaction is typically conducted by stirring the compound of formula (IV) together with the above recited reagents in a polar solvent at a temperature of about 20° C. to about 150° C. under an atmosphere of ethylene at a pressure of about 1 atmosphere to about 10 atmospheres. The preferred polar solvents for use in this reaction include, but are not limited to ethers, such as tetrahydrofuran, dimethoxyethane and dioxane; lower trialkylamines, such as triethylamine, diisopropylethylamine and tributylamine; aromatic hydrocarbons, such as benzene, toluene and xylene; dimethylformamide; N-methyl-2-pyrrolidone; acetonitrile; dimethylacetamide; or a mixture of any of these solvents. Acetonitrile is an especially preferred solvent.

The compounds of formula (I),

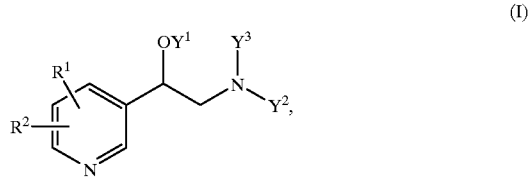

wherein $R^1$ and $R^2$ are as defined hereinabove and $Y^1$, $Y^2$ and $Y^3$ are chemical substituents which can be attached to the atoms to which they are attached are β-adrenergic receptor agonists and as such have utility as hypoglycemic and antiobesity agents. Examples of such substituents and the resultant β-adrenergic receptor agonists can be found in PCT Publication No. WO 94/29290 published Dec. 22, 1994.

Compounds of formula (XIV) can be prepared from compounds of formula (I) wherein $R^1$ is —NHCO($C_1$–$C_6$) alkyl; $R^2$ and $Y^3$ are each H and $Y^2$ is

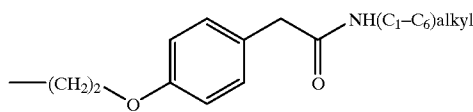

by reacting said compound of formula (I) with an acylating agent such as an acid anhydride of the formula (($C_1$–$C_6$) alkyl-CO)$_2$O, an acid chloride of the formula ($C_1$–$C_6$)alkyl-COCl or a dicarbonate of the formula (($C_1$–$C_6$)alkyl-O—CO)$_2$—O in a reaction inert solvent at a temperature of about 0° C. to about 150° C. for 1 to 48 hours. Suitable reaction inert solvents for this reaction include aromatic hydrocarbons including but not limited to benzene, toluene and xylene; dimethylsulfoxide; N,N-dimethylformamide; chlorinated hydrocarbons including but not limited to methylene chloride, chloroform and carbon tetrachloride; ether solvents such as diethyl ether, tetrahydrofuran and dioxane or any mixture of these solvents. When a dicarbonate is used as the acylating agent, it is generally preferred to use a mixture of toluene and dimethylsulfoxide as the solvent mixture. Preferably this reaction is carried out at a temperature of about 70° C. to 95° C.

The compound of formula (XIII) can be prepared from the compounds of formula (XIV) by reacting said compounds of formula (XIV) with an aqueous acid such as sulfuric acid, hydrochloric acid and the like at a temperature of about 25° C. to about 100° C. for one hour to forty-eight hours. Preferably, the aqueous acid is hydrochloric acid and the reaction temperature is maintained at about 90° C. to about 100° C. for about twenty-four hours.

It will be appreciated by those skilled in the art that the compounds of formulae (II) and (VI) contain at least one chiral center. Accordingly, those compounds may exist in, and be isolated in, optically active and racemic forms. Some compounds may exhibit polymorphism. It is to be understood that the present invention encompasses any racemic, optically active, polymorphic or stereoisomeric form, or any mixture thereof, which form possesses properties useful in the treatment of the diseases or conditions noted herein or useful as intermediates in the preparation of any compounds useful in the treatment of said diseases or conditions, it being well known in the art how to prepare optically active forms (for example, by resolution of the racemic form by recrystallization techniques, by synthesis from optically active starting materials, by chiral synthesis or by chromatographic separation using a chiral stationary phase) and how to determine efficacy for the treatment of said utilities. In general, (R)-stereochemistry is preferred at all chiral centers in the compounds disclosed in this invention.

Conventional methods and techniques of purification and separation known to those skilled in the art may be used to isolate the compounds of this invention. Such techniques include all types of chromatography, including but not limited to high performance liquid chromatography, column chromatography using common adsorbents such as silica gel, thin layer chromatography and the like; recrystallization; and differential (i.e., liquid-liquid) extraction techniques.

As used in the specification and appendant claims the following terms have the meanings described. The terms alkyl and alkoxy include both straight and branched chain radicals, but it is to be understood that references to individual radicals such as propyl or propoxy embrace only the straight chain radical unless reference is specifically made to for example isopropyl or isopropoxy, in which case the branched chain isomer is meant.

The term halo, unless otherwise indicated, includes chloro, flouro, bromo and iodo.

The terms "Ad-mix-A" and "Ad-mix-α" are synonymous names for a reagent used in this invention and sold by Aldrich Chemical Co. The reagent contains the chiral ligand $(DHQ)_2PHAL$, the catalyst potassium osmate (VI) dihydrate, the auxiliary oxidizing agent potassium ferricyanide and the base potassium carbonate. The reagent is used in the asymmetric dihydroxylation of olefins. The reagent is sold by Aldrich under a license from Sepracor, Inc. of Marlborough, Mass. (see Aldrich catalog, 1996–97, page 444).

The terms "Ad-mix-B" and "Ad-mix-β" are synonymous names for a reagent used in this invention and sold by Aldrich Chemical Co. The reagent contains the chiral ligand $(DHQD)_2PHAL$, the catalyst potassium osmate (VI) dihydrate, the auxiliary oxidizing agent potassium ferricyanide and the base potassium carbonate. The reagent is used in the asymmetric dihydroxylation of olefins. The reagent is sold by Aldrich under a license from Sepracor, Inc. of Marlborough, Mass. (see Aldrich catalog, 1996–97, page 444).

The term "protected amino" includes an amine nitrogen atom, e.g., $RNH_2$ or $R_2NH$, to which a protecting group is attached. The term "protecting group" defines an organic radical which is readily attached to and detached from said nitrogen atom, where said group is not susceptible to reaction with or degeneration by other substrates or reagents used to transform other functional groups within the molecule to which said nitrogen atom is attached or intermediates or transition state molecules formed during such reactions. Said protecting group is readily attached and removed under mild conditions. Preferred protected amino groups include $(C_1-C_8)$alkylamino, $-NR^3CO(CH_2)_pR^0$, $-NR^3CO_2R^0$ and $-NR^3SO_2(CH_2)_pR^0$ wherein $R^0$, $R^3$ and p are as defined hereinabove.

The term "suitable leaving group" includes a group which may be readily displaced by a nucleophile which has a greater affinity for the positively charged carbon atom to which said leaving group is attached than said leaving group. Preferred leaving groups are chloro and organosulfonyloxy groups. Particularly preferred leaving groups are organosulfonyloxy groups. Particularly preferred organosulfonyloxy groups are methanesulfonyloxy, benzenesulfonyloxy, p-toluenesulfonyloxy, p-nitrobenzenesulfonyloxy or m-nitrobenzenesulfonyloxy.

The term "suitable base" includes a base which, when added to the reaction mixture in which said base is to operate, increases the pH of the reaction mixture or operates on the substrate to remove a proton from said substrate or otherwise render said substrate susceptible to electrophilic attack without affecting other potentially reactive functional groups in said substrate.

The expression "pharmaceutically-acceptable acid addition salts" is intended to include but not be limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

The acid addition salts of the compounds of the present invention are readily prepared by reacting the base forms of the compounds disclosed in this invention with an appropriate acid. When the salt is of a monobasic acid (e.g., the hydrochloride, the hydrobromide, the p-toluenesulfonate, the acetate) the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are conveniently combined in a co-solvent from which the desired salt precipitates or can otherwise be isolated by concentration and addition of a non-solvent or by simple addition of a non-solvent without concentration or by lyophilization of an aqueous solution of said salt.

If not commercially available, the necessary starting materials for the chemical reactions disclosed herein may be prepared by procedures which may be selected from standard organic chemical techniques found in standard organic textbook references. The techniques found therein may be applied directly to the synthesis of known starting materials described directly in that reference or may be applied by analogy to compounds having similar functionality to achieve predictable results.

In the Examples which follow, common chemical acronyms and abbreviations are used. These acronyms and abbreviations include BOC, meaning tert-butoxycarbonyl; Cbz, meaning benzyloxycarbonyl; THF, meaning tetrahydrofuran; DMF, meaning dimethylformamide; NMP, meaning N-methyl-2-pyrrolidinone; DMAC, meaning N,N-dimethylacetamide; DME, meaning 1,2-dimethoxyethane; DMSO, meaning dimethylsulfoxide; and TFA, meaning trifluoroacetic acid. Where used, the term "lower alkyl" means $C_1-C_4$. By analogy, the the terms lower alkoxy, lower alkanoyloxy and lower acyloxy refer to groups containing one to four carbon atoms.

The present invention is illustrated by the following Examples. However, it should be understood that the invention is not limited to the specific details of these Examples.

EXAMPLE ONE

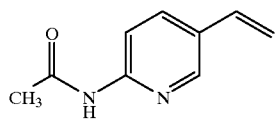

N-(5-Vinyl-pyridin-2-yl)-acetamide

A solution of of N-(5-bromo-pyridin-2-yl)-acetamide (4.30 g, 20 mmol) in acetonitrile (15 ml) and triethylamine (5.04 ml) was treated with palladium acetate (45 mg, 0.2 mmol) and tri-o-tolylphosphine (203 mg, 0.66 mmol). The mixture was placed in a pressure reactor under 50 psig of ethylene pressure and heated at 85° C. for 66 hours. The reaction mixture was cooled, vented, and partitioned between phosphate buffer (0.1 M, pH 6.6) and ethyl acetate. The aqueous phase was extracted with ethyl acetate twice more. The combined ethyl acetate extracts were washed with additional phosphate buffer, brine and dried over sodium sulfate. The extracts were filtered and evaporated to afford 2.06 g (63%) of the title product as a flaky crystalline residue. Recrystallization from ethyl acetate/cyclohexane gave colorless flakes. mp 120–121° C. 1H NMR (CDCl$_3$): δ=8.55 (br, 1 H); 8.24 (d, 1 H); 8.15 (d, 1 H); 7.76 (d of d, 1H); 6.64 (d of d, 1 H); 5.73 (d, 1 H); 5.28 (d, 1 H); 2.19 (s, 3 H). MS (Cl): m/z=163 (M+H$^+$).

EXAMPLE TWO

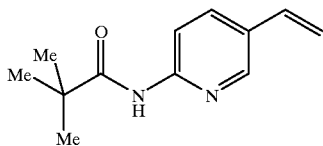

N-(5-Vinyl-pyridin-2-yl)-2,2-dimethylpropionamide

A solution of N-(5-bromopyridin-2-yl)-2,2-dimethylpropionamide (5.60 g, 21.8 mmol) in acetonitrile (20 ml) and triethylamine (5.49 ml) was treated with palladium acetate (177 mg, 0.8 mmol) and tri-o-tolylphosphine (795 g, 2.6 mmol). The mixture was placed in a pressure reactor under 130 psig of ethylene pressure and heated at 85° C. for 18 hours. The reaction mixture was cooled, vented, diluted with ethyl acetate and filtered. The ethyl acetate solution was washed sequentially with dilute citric acid, water and brine and then dried over sodium sulfate. The dried solution was filtered and evaporated. Chromatography of the residue on silica gel, eluting with dichloromethane/ethyl acetate (24:1) afforded 3.92 g (88%) of the title product as an oil. $^1$H NMR (CDCl$_3$): δ=8.21 (m, 2 H); 8.03 (br, 1 H); 7.76 (d of d, 1 H); 6.63 (d of d, 1 H); 5.71 (d, 1 H); 5.25 (d, 1 H); 1.29 (s, 9H). MS (Cl): m/z=205 (M+H$^+$).

EXAMPLE THREE

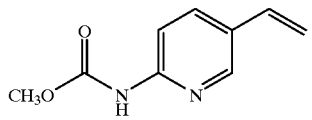

N-(5-Vinyl-pyridin-2-yl)-carbamic acid methyl ester

A solution of (5-bromo-pyridin-2-yl)-carbamic acid methyl ester (1.68 g, 7.2 mmol) in acetonitrile (15 ml) and triethylamine (1.84 ml) was treated with palladium acetate (65 mg, 0.29 mmol) and tri-o-tolylphosphine (295 mg, 0.97 mmol). The mixture was placed in a pressure reactor under 130 psig of ethylene pressure and heated at 85° C. for 18 hours. The reaction mixture was cooled, vented and diluted with ethyl acetate and filtered. The ethyl acetate solution was washed sequentially with 1M aqueous citric acid, water, brine and was dried over sodium sulfate and filtered. The filtrate was evaporated. The residue was recrystallized from dichloromethane-hexane to afford 0.759 g (58%) of the title product as colorless crystals. mp 146–148° C. $^1$H NMR (CDCl$_3$): δ=9.04 (br, 1 H); 8.28 (d, 1 H); 7.97 (d, 1 H); 7.77 (d of d, 1 H); 6.64 (d of d, 1 H); 5.71 (d, 1 H); 5.26 (d, 1 H); 3.81 (s, 3H). MS (Cl): m/z=179 (M+H$^+$).

EXAMPLE FIVE

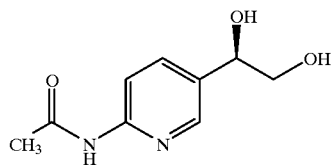

(R)-N-(5-(1,2-Dihydroxy-ethyl)-pyridin-2-yl)-acetamide

A suspension of AD-Mix-B® (56.33 g) in water (200 ml) and t-butanol (200 ml) was cooled to 5° C. and N-(5-Vinyl-pyridin-2-yl)-acetamide (6.52 g, 40.2 mmol) was added followed by 2-propanol (400 ml). The mixture was stirred at 5° C. for 12 hours and then at 20° C. for 12 hours. The reaction mixture was then treated with sodium sulfite (60.4 g), stirred for 30 minutes and then diluted with 500 ml of 2-propanol and stirred for an additional one hour. The mixture was filtered and the alcoholic phase was separated and evaporated to dryness. The residue was slurried in 500 ml of 2-propanol and evaporated again. The residue was dried to afford 6.35 g (80%) of the title product as colorless crystals. The crystals were recrystallized by dissolving in hot glacial acetic acid, diluting 7-fold with 2-propanol, cooling and seeding to give the title product as crystals. mp 184–185° C. $^1$H NMR (dmso-d$_6$): δ=8.22 (d, 1 H); 7.99 (d, 1 H); 7.68 (d of d, 1 H); 4.52 (t, 1 H); 3.44 (m, 2 H); 2.07 (s, 3 H). MS (Cl): m/z=197 (M+H$^+$). Optical Rotation: −4.52° (c=0.05, acetic acid). Analysis: Calculated for C$_9$H$_{12}$N$_2$O$_3$: C, 55.09%; H,6.17%; N, 14.28%. Found: C, 55.43%; H, 5.97%; N, 13.96%.

EXAMPLE SIX

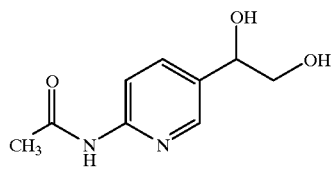

(R,S)-N-(5-(1,2-Dihydroxy-ethyl)-pyridin-2-yl)-acetamide

A vigorously stirred mixture of potassium carbonate (25.56 g, 185 mmol), potassium ferricyanide (60.9 g, 185 mmol) and N-(vinyl-pyridin-2-yl)-acetamide (100.0 g, 61.6 mmol) in water (120 ml) and 2-propanol (120 ml) was

EXAMPLE SEVEN

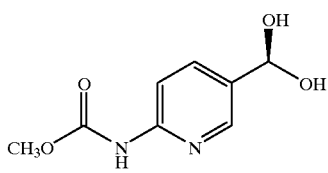

(R)-N-(5-(1,2-(Dihydroxy-ethyl)-pyrdin-2-yl)-carbamic acid methyl ester

A suspension of AD-Mix-B® (2.80 g) in water (10 ml) and t-butanol (10 ml) was cooled to 5° C. and N-(5-vinyl-pyridin-2-yl)-carbamic acid methyl ester (0.356 g, 2.0 mmol) was added. The mixture was stirred at 5° C. for 18 hours. The reaction mixture was then treated with sodium sulfite (3.0 g), stirred for an additional 30 minutes and then extracted three times with ethyl acetate. The ethyl acetate extracts were combined and washed with water and brine and dried and evaporated to afford 0.410 g (96%) of the title product as colorless crystals. mp 153–154° C. $^1$H NMR (CDCl$_3$): δ=8.90 (br, 1 H); 8.09 (d, 1 H); 7.75 (d, 1 H); 7.53 (d of d, 1 H); 4.55 (m, 1 H); 3.60 (s, 3 H); 3.47 (m, 1 H); 3.41 (m, 1 H). MS (Cl): m/z=213 (M+H$^+$).

EXAMPLE EIGHT

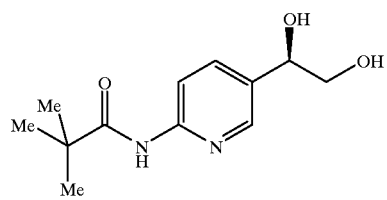

(R)-N-(5-(1,2-Dihydroxy-ethyl)-pyrdin-2-yl)-2,2-dimethylpropionamide

A suspension of AD-Mix-B® (1.40 g) in water (5 ml) and t-butanol (5 ml) was cooled to 5° C. and N-(5-vinyl-pyridin-2-yl)-2,2-dimethylpropionamide (0.204 g, 1.0 mmol) was added. The mixture was stirred at 5° C. for 18 hours. The reaction mixture was then treated with sodium sulfite (3.0 g), stirred for 30 minutes and then extracted with dichloromethane. The dichloromethane extract was washed with water and brine and then dried and evaporated to afford 0.230 g (96%) of the title product as colorless crystals. mp 105–106° C. $^1$H NMR (CDCl$_3$): δ=8.21 (br, 1 H); 8.10 (m, 2 H); 7.61 (d of d, 1 H); 4.70 (m, 1 H); 3.64 (m, 1 H); 3.57 (m, 1 H); 1.25 (s, 9 H). MS (Cl): m/z=239 (M+H$^+$).

treated with potassium osmate (VI) dihydrate (46 mg, 0.123 mmol) at 25° C. The mixture was then stirred for one hour. The mixture was separated and the aqueous phase was extracted three times more with 120 ml portions of 2-propanol. The residue from the aqueous phase was triturated with hot 2-propanol. The 2-propanol extracts were combined, concentrated and azeotropically dried with 2-propanol. The residue was triturated with ether, filtered, washed with ether and dried to afford 10.61 g (87%) of the title product as an off white solid. mp 160–162° C. $^1$H NMR (dmso-d$_6$): δ=8.22 (d, 1 H); 7.99 (d, 1 H); 7.68 (d of d, 1 H); 4.52 (t, 1 H); 3.44 (m, 2 H); 2.07 (s, 3 H). MS (Cl): m/z=197 (M+H$^+$).

EXAMPLE NINE

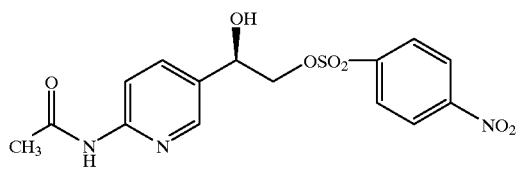

(R)-4-Nitro-benzenesulfonic acid 2-(6-acetylamino-pyridin-3-yl)-2-hydroxy-ethyl ester A solution of (R)-(5-(1,2-dihydroxy-ethyl)-pyridin-2-yl)-acetamide (0.294, 1.5 mmol) in anhydrous DMF (3 ml) was treated with triethylamine (0.63 g, 4.5 mmol) and cooled to −40° C. A solution of 4-nitrobenzenesulfonyl chloride (0.332 g, 1.5 mmol) in ethyl acetate (3 ml) was added dropwise. After 45 minutes at −45° C., the mixture was stirred for one hour at 20° C. The mixture was then diluted with ethyl acetate and washed sequentially with water, twice with pH 6.6 buffer (0.1 M phosphate), water and brine. The ethyl acetate layer was dried over sodium sulfate, filtered and evaporated. The residue was triturated with 1,2-dichloroethane to give 0.381 g (67%) of the title product as colorless crystals. mp 116–120° C. with decomposition. $^1$H NMR (dmso-d$_6$): δ=8.36 (d, 2 H); 8.16 (d, 1 H); 8.04 (d, 2 H); 7.91 (d, 1 H); 7.62 (d of d, 1 H); 5.89 (d, 1 H); 4.81 (d of d, 1 H); 4.24 (d, 2 H); 2.06 (s, 3 H). MS (Cl): m/z=179 (M+H$^+$-O$_2$NC$_6$H$_4$SO$_3$H).

EXAMPLE TEN

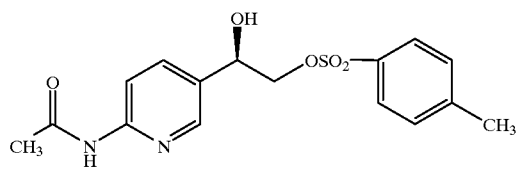

(R)-Toluene-4-sulfonic acid 2-(6-acetylamino-pyridin-3-yl)-2-hydroxy-ethyl ester A slurry of (R)-N-(5-(1,2-dihydroxy-ethyl)-pyridin-2-yl)-acetamide (71.2 g, 362 mmol) in anhydrous pyridine (362 ml) was cooled to 5° C. and treated with p-toluenesulfonyl chloride (69.18 g, 362 mmol) in one portion. The reaction mixture was stirred at 5° C. for 20 minutes, then the cooling bath was removed and the mixture was stirred at ambient temperature for two hours. The mixture was then concentrated, dissolved in 30 ml of methanol, concentrated and dissolved in toluene (300 ml) and concentrated again. The residue was treated again with methanol and toluene, then the residue was dissolved in ethyl acetate and washed sequentially with half-saturated brine, brine and dried over sodium sulfate. The filtrate was evaporated to afford 102.2 g (80%) of the title product as light buff crystals. Recrystallization from ethanol-cyclohexane afforded the title product as colorless crystals. mp 124–126° C. $^1$H NMR (dmso-d$_6$): δ=10.5 (br, 1 H); 8.21 (d, 1 H); 7.94 (d, 1 H); 7.68 (d, 2 H); 7.51 (d of d, 1 H); 7.41 (d, 1 H); 5.87 (d, 1 H); 4.76 (d of d, 1 H); 4.05 (d, 2 H); 2.41 (s, 3 H); 2.10 (s, 3 H). MS (Cl): m/z=351 (M+H$^+$). Optical Rotation: −36.181° (c=1.19, acetone). Analysis: Calculated for C$_{16}$H$_{18}$N$_2$O$_5$S: C, 54.85%; H, 5.18%; N, 7.99%. Found: C, 54.91%; H, 5.34%; N, 8.06%.

EXAMPLE ELEVEN

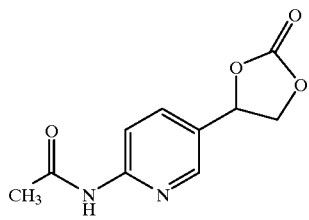

N-(5-(2-Oxo-[1,3]dioxolan-4-yl)-pyridin-2-yl)-acetamide

A solution of (R,S)-N-(5-(1,2-dihydroxy-ethyl-pyridin-2-yl)-acetamide (0.392 g, 2 mmol) and 1,1'-carbonyldiimidazole (0.648 g, 4 mmol) in DMF (3 ml) was stirred at 20° C. for six hours and then concentrated under high vacuum. The residue was treated with water and ethyl acetate. The ethyl acetate was separated and the aqueous phase was extracted three additional times with ethyl acetate. The combined ethyl acetate extracts were washed with brine, dried, filtered and concentrated. Chromatography of the residue on silica gel, eluting with dichloromethane/methanol (1:1) afforded 0.078 g (17%) of the title product as white crystals. mp 135–139° C. $^1$H NMR (dmso-d$_6$): δ=8.41 (d, 1 H); 8.11 (d, 1 H); 7.93 (d of d, 1 H); 5.85 (t, 1 H); 4.84 (t, 1 H); 4.47 (t, 1 H); 2.09 (s, 3 H). MS (Cl): m/z=223 (M+H$^+$).

EXAMPLE TWELVE

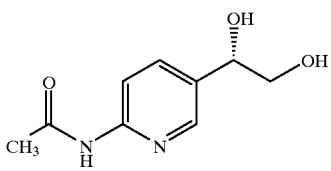

(S)-N-(5-(1,2-Dihydroxy-ethyl)-pyridin-2-yl)-acetamide

A suspension of AD-Mix-α® (35 g) in water (50 ml) and 2-propanol (50 ml) was cooled to 0° C. and N-(5-Vinyl-pyridin-2-yl)-acetamide (4.05 g, 25 mmol) was added. The mixture was stirred overnight at 20° C. The reaction mixture was then treated with sodium sulfite (37.5 g). The 2-propanol was decanted. The residue was diluted with 2-propanol (50 ml) and refluxed and the 2-propanol was decanted. This process was repeated three times. The alcoholic portions were combined, filtered and the filtrate was concentrated to afford a yellow solid. This solid was reslurried in hot 2-propanol (20 ml) and filtered to afford 3.80 g of impure product. This was dissolved in hot ethyl acetate (6 ml). Acetonitrile (42 ml) was added. The solution was cooled to precipitate the product. The suspension was stirred overnight and filtered to afford 3.0 g (61%) of an off-white solid. $^1$H NMR (dmso-d$_6$): δ=8.22 (d, 1 H); 7.99 (d, 1 H); 7.68 (d of d, 1 H); 4.52 (t, 1 H); 3.44 (m, 2 H); 2.07 (s, 3 H). ms (Cl): m/z=197 (M+H$^+$).

EXAMPLE THIRTEEN

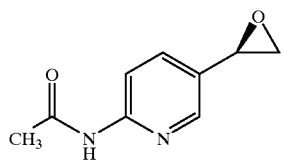

(R)-N-(5-Oxiranyl-pyridin-2-yl)-acetamide

A solution of (R)-toluene-4-sulfonic acid 2-(6-acetylamino-pyridin-3-yl)-2-hydroxy-ethyl ester (200 g, 0.57 mol) in THF (2.4 L) was cooled to −15° C. and potassium t-butoxide (542 ml, 0.542 mol, 1M in THF) was added slowly at −15° C. to −10° C. over a two hour period. Stirring was continued at −15° C. for an additional 40 minutes. The reaction mixture was filtered with the aid of Celite®. The filtration was done through cloth precoated with Celite®. The filter cake was washed with tetrahydrofuran. The filtrate was concentrated under vacuum to afford 300 ml of an oil. The oil was diluted with 1.2 liters of hexanes which resulted in the formation of a solid. The suspension was stirred at room temperature for one hour to granulate the solid. The suspension was filtered and the filtrate was washed with hexanes to afford 80.0 g (78.8%) of the title product as a solid. mp 96–98° C. $^1$H NMR (CDCl$_3$): δ=8.70 (br, 1 H); 8.21 (m, 2 H); 7.57 (d of d, 1 H); 3.86 (m, 1 H); 3.17 (m, 1 H); 2.83 (m, 1 H); 2.19 (s, 3 H). MS (Cl): m/z=179 (M+H$^+$).

EXAMPLE FOURTEEN

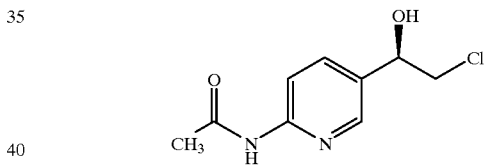

(R)-N-(5-(2-Chloro-1-hydroxy-ethyl)-pyridin-2-yl)-acetamide

A mixture of (R)-N-(5-(2-chloro-1-hydroxy-ethyl)-pyridin-2-yl)-acetamide and (R)-toluene-4-sulfonic acid 2-(6-acetylamino-pyridin-3-yl)-2-hydroxy-ethyl ester (86.3 g) was dissolved in 604 ml of ethanol. The solution was heated to obtain a clear solution and then lithium chloride (10.3 g, 0.243 mol) was added. The reaction mixture was heated under reflux overnight. Additional lithium chloride (2.0 g) was added and the reaction was heated under reflux for an additional two days. The reaction mixture was cooled and concentrated in vacuum. The residue was partitioned between ethyl acetate and half-saturated brine. The layers were separated and the ethyl acetate layer was washed once with saturated brine. The aqueous layers were combined and extracted once with ethyl acetate. The ethyl acetate layers were combined and dried with MgSO4 then concentrated to an oil. The residue was dissolved in tetrahydrofuran to obtain a hazy solution. This solution was treated with charcoal and silica gel, stirred warm for 30 minutes and filtered. The filter cake was washed with tetrahydrofuran and the solution was concentrated to a semi-solid. The semi-solid was dissolved in 500 ml of ethyl acetate, washed with half-saturated brine, once with saturated aqueous sodium bicarbonate and once with saturated aqueous sodium chloride. The ethyl acetate layer was concentrated to afford an oil. The resulting suspension was slurried in methylene chloride (100 ml), cooled then vacuum filtered to afford 29 g of title chloride compound. $^1$H NMR (DMSO-d$_6$): δ=10.48 (br s, 1H); 8.29 (d, 1H); 8.00 (d, 1H); 7.73 (d of d, 1H); 5.88 (d, 1H); 4.76 (m, 1H); 3.72 (m, 1H); 2.06 (s, 3H).

EXAMPLE FIFTEEN

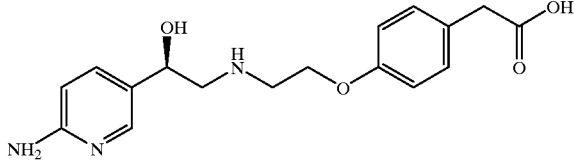

(4-(2-(2-(6-Aminopyridin-3-yl)-2-(R)-hydroxyethylammonium)-ethoxy)-phenyl)-acetate A mechanically stirred slurry of the title compound of Example Thirteen (50.0 gm, 0.2806 mol, 1.0 eq) and the title compound of Preparation Seven (99.4 gm, 0.477 mol, 1.7 eq) in 5.1 (vol/vol)::Toluene:DMSO (375 mL) was heated on a steam bath. The slurry became homogenous at about 70° C., and the temperature was maintained at 90–95° C. for 3 to 16 hrs. The solution was cooled to 10–15°. This resulted in the formation of a precipitate. Di-t-butyldicarbonate (129 mL, 0.561 mol, 2.0 eq) was added dropwise over a one hour period. The resulting homogenous solution was stirred at room temperature overnight. The solution was poured into a mixture of ethyl acetate (1L) and water (850 mL). After stirring for 10 min, the phases were allowed to separate, at which time a heavy red oil fell out into the aqueous layer. The aqueous layer, with oil, was removed. The organic layer was washed with water (500 mL) and concentrated to an amber oil. This amber oil was taken up in 6N HCl (300 mL) and heated on the steam bath overnight. The solution was cooled to room temperature, and the solids which precipitated were filtered. (These solids are the amino acid of the excess side chain which was used in the coupling with the epoxide.) The acidic solution containing the title compound was concentrated under vacuum to a semi-solid. The semi-solid was treated with water and then reconcentrated (twice) to remove excess HCl. The solid was dissolved in water and brought to pH 7 with potassium hydroxide. The solid which precipitated was filtered and washed first with water and then with THF. The solids were dried on the filter funnel to a weight of 22.5 gm. The crude solid was redissolved in 30 volumes of 90° C. water and treated with decolorizing carbon. After filtration to remove the carbon, the filtrate was cooled and concentrated by evaporation of some of the water. The precipitate which formed was filtered to provide 9.5 gm of the title compound. NMR (400 MHz, DMSO-d$_6$+ D$_2$O): d=7.79 (d, 1H, J=1.87), 7.34–7.32 (m, 1H), 7.11 (d, 2H, J=8.51), 6.79 (d, 2H, J=8.51). 6.41 (d, 1H, J=8.51), 4.54–4.51 (m, 1H), 4.01–3.99 (m, 2H), 3.35 (s, 2H), 2.97–2.94 (m, 2H), 2.79–2.69 (m, 2H). MS (APCl) m/z 332.2 (MH$^+$), 314.2, 159.1, 156.9.

PREPARATION ONE

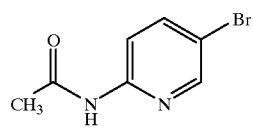

N-(5-Bromo-pyridin-2-yl)-acetamide

A solution of 2-amino-5-bromopyridine (25.0 g, 144 mmol) in acetic acid (50 ml) and acetic (25.0 g, anhydride (250 ml) was heated at reflux for two hours. The reaction mixture was then cooled and poured into water (750 ml) with stirring. After one hour, the solution was adjusted to pH 10 with 50% sodium hydroxide and the precipitate was filtered, washed with water and dried to give 26.5 g (85%) of the title product as a white flaky solid. mp 175–176° C. $^1$H NMR (CDCl$_3$): δ=8.29 (d, 1 H); 8.12 (d, 1 H); 7.96 (br, 1 H); 7.78 (d of d, 1 H); 2.19 (s, 3 H). MS (EI): m/z=214, 216 (M$^+$, Br isotopes).

PREPARATION TWO

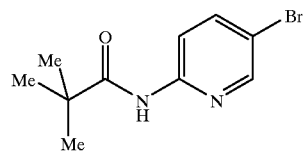

N-(5-Bromo-pyridin-2-yl)-2,2-dimethylpropionamide

A solution of trimethylacetyl chloride (17.5 g, 146 mmol) in dichloromethane (25 ml) was added to a solution of 2-amino-5-bromopyridine (25.0 g, 144 mmol) in dichloromethane (100 ml) and triethylamine (24 ml) dropwise with stirring at 20° C. The reaction mixture was then stirred for 40 minutes, filtered, washed with water, dried and concentrated. Recrystallization from hexanes afforded 20.6 g (70%) of the title product as a white flaky solid. mp 63–64° C. $^1$H NMR (CDCl$_3$): δ=8.82 (br, 1 H); 8.30 (d, 1 H); 8.19 (m, 2 H); 1.36 (s, 3 H). MS (EI): m/z=256, 258 (M$^+$, Br isotopes).

PREPARATION THREE

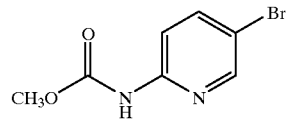

N-(5-Bromo-pyridin-2-yl)-carbamic acid methyl ester

A solution of 2-amino-5-bromopyridine (9.46 g, 20 mmol) and N,N-diisopropylethylamine (3.10 g) in chloroform (20 ml) was added to a solution of methyl chloroformate (2.30 g, 24 mmol) in chloroform (25 ml) dropwise with stirring at 0° C. The reaction mixture was stirred for 20 minutes, filtered and the precipitate was washed with chloroform and dried to afford 1.71 g (37%) of the title product as a white solid. mp 191–192° C. $^1$H NMR (CDCl$_3$): δ=8.42 (d, 1 H); 8.30 (d, 1 H); 7.91 (d, 1 H); 7.77 (d of d, 1 H); 3.79 (s, 3 H). MS (EI): m/z=230, 232 (M$^+$, Br isotopes).

PREPARATION FOUR

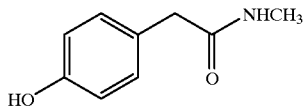

N-Methyl 4-hydroxyphenylacetamide

Monomethylamine (22.43 kg, 722.15 mol, 6 eq.) was added over a 7-hour period to a solution of methyl-4-hydroxyphenylacetate (20.0 kg, 120.35 mol, 1.0 eq.) in methanol (31.7 gal) and stirred overnight at room temperature. Methanol was then displaced under vacuum with ethyl acetate. The resulting slurry (ca. 20 gal) was stirred at +10° C. for 1 hour, then filtered and dried under vacuum at 45° C. to yield of the title compound(18.68 kg, 94% of theory). mp 124–125° C. NMR (300 MHz, $d_6$-DMSO): δ=9.26 (s, 1H), 8.00–7.65 (br s, 1H), 7.21–6.90 (m, 2H), 6.86–6.55 (m, 2H), 3.26 (s, 2H), 2.75–2.45 (m, 3H).

PREPARATION FIVE

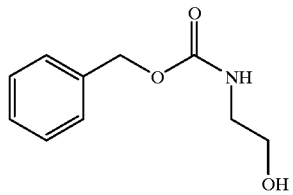

N-Benzyloxycarbonyl-2-aminoethanol

Benzylchloroformate (44.95 kg, 263.5 mol, 1.0 eq.) was added over a 2 hour period at room temperature to a solution of ethanolamine (16.1 kg, 263.5 mol, 1.0 eq.) in water (34 gal). After stirring for 30 minutes, this was added to a cold (5–10° C.) solution of $NaHCO_3$ (33.2 kg, 395.25 mol, 1.5 eq) in $H_2O$ (330 L) over a 30 min period and then allowed to stir at room temperature overnight. Ethyl acetate (22 gal) was added, the layers separated, and the aqueous layer extracted again with 22 gal. ethyl acetate. The combined organic extracts were concentrated under vacuum to a volume of 10 gal, and the remainder displaced with isopropyl ether. The resulting slurry was stirred and cooled to +10° C. for 2 hours, then filtered. The solids were washed with isopropyl ether and vacuum dried to give the title compound (39.1 kg, 71.1%). mp 61–63° C. NMR (300 MHz, $d_6$-DMSO): δ=7.50–7.37 (m, 5H), 7.37–7.16 (m, 1H), 5.05 (s, 2H), 4.70–4.63 (m, 1H), 3.46–3.37 (m, 2H), 3.13–3.03 (m, 2H).

PREPARATION SIX

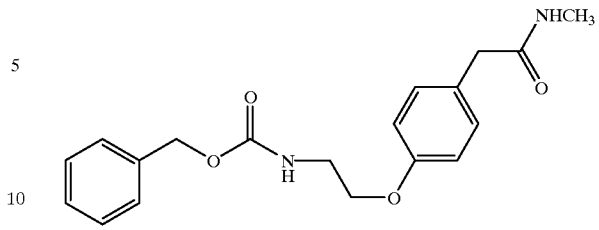

Methyl 4-(2-(N-benzyloxycarbonylamino)ethoxy) phenylacetamide

The title compound of Preparation Four (18.68 kg, 113.14 mol, 1.0 eq.) and the title compound of Preparation Five (33.13 kg, 169.75 mol, 1.5 eq.) were dissolved in THF (40 gal). Triphenylphosphine (44.5 kg, 169.75 mol, 1.5 eq.) was added and the mixture cooled to −5° C. Diisopropyl azodicarboxylate (34.3 kg, 169.75 mol, 1.5 eq.) was added over an 8 hour period, and the reaction allowed to warm to room temperature overnight. Ethyl acetate (20 gal) was added to the resulting white slurry, stirring was continued for 6 hours, and the solids filtered off and dried to yield crude title compound. (29.6 kg, 76.5% of theory, mp 131–133° C.). The crude product was slurried in ethyl acetate (39.1 gal) for 3 hours at +10° C., then filtered, washed with 14 gal 10° C. ethyl acetate, and vacuum dried to yield the title compound (26.1 kg, 88.2% recovery, 67.5% overall). mp 134–136° C. NMR (300 MHz, $d_6$-DMSO): δ=7.98–7.82 (m, 1H), 7.58–7.49 (m, 1H), 7.42–7.28 (m, 5H), 7.20–7.10 (d, 2H), 6.90–6.80 (d, 2H), 5.06 (s, 2H), 4.02–3.93 (m, 2H), 3.47–3.29 (m, 4H), 2.62–2.54 (d, 3H).

PREPARATION SEVEN

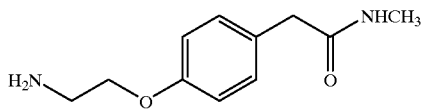

Methyl 4-(2-aminoethoxy)phenylacetamide

The title compound of Preparation Six (18.4 kg, 53.73 mol) and 1.84 kg 10% palladium on carbon (50% $H_2O$ wet) were suspended in 73 gal methanol under nitrogen, and the reaction vessel pressurized to 50 psig with hydrogen gas. This $H_2$ pressure was maintained by additional charges of $H_2$ until there was no further uptake of $H_2$ (approx. 20 hours) and the reaction was complete by tlc. After purging the vessel with $N_2$, the mixture was heated to 45° C. and filtered at this temperature through Celite. The solvent was displaced with toluene until a final volume of 8 gal was achieved. After cooling to +5° C. the resulting solids were filtered off, washed with cold toluene, and vacuum dried to give the title compound (9.95 kg, 88.9% of theory). NMR (300 MHz, $d_6$-DMSO): δ=7.99–7.57 (m, 1H), 7.20–7.10 (d, 2H), 6.90–6.80 (d, 2H), 3.93–3.83 (m, 2H), 3.30 (s, 2H), 3.00–2.62 (m, 4H), 2.57 (d, 2H).

What is claimed is:

1. A compound of the formula

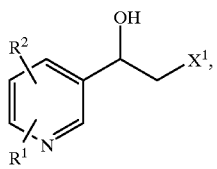

wherein:

$R^1$ is selected from the group consisting of nitro, amino and protected amino;

$R^2$ is selected from the group consisting of H, fluoro, chloro, $CF_3$, nitro, $(C_1-C_4)$alkyl, $(C_1-C_4)$alkoxy, amino and protected amino;

$X^1$ is OH or a suitable leaving group;

racemic mixtures thereof;

R enantiomers thereof, wherein said R enantiomers are essentially free of their corresponding S enantiomers; and S enantiomers thereof, wherein said S enantiomers are essentially free of their corresponding R enantiomers.

2. A compound of claim 1 wherein $X^1$ is OH.

3. A compound of claim 2 wherein said protected amino, for each occurrence, is independently selected from the group consisting of $(C_1-C_8)$alkylamino, $-NR^3CO(CH_2)_p R^0$, 13 $NR^3CO_2R^0$ and $-NR^3SO_2(CH_2)_p R^0$;

$R^3$, for each occurrence, is independently H or $(C_1-C_6)$alkyl;

$R^0$, for each occurrence, is independently $(C_1-C_{10})$alkyl, phenyl or phenyl independently substituted by one to three $(C_1-C_4)$alkyl, $(C_1-C_4)$alkoxy or halo; and p is 0, 1 or 2.

4. A compound of claim 3 wherein $R^2$ is H.

5. A compound of claim 4 wherein $R^1$ is amino, $-NR^3CO(C_1-C_{10})$alkyl, $-NR^3CO_2(C_1-C_8)$alkyl or $-NR^3CO(CH_2)_p R^0$.

6. A compound of claim 5 wherein $R^1$ is amino or $-NR^3CO(C_1-C_{10})$alkyl.

7. The compound of claim 6 which is N-(5-(1,2-dihydroxyethyl)-pyridin-2-yl)-acetamide.

8. The R enantiomer of the compound of claim 7, essentially free of its corresponding S enantiomer.

9. The S enantiomer of the compound of claim 7, essentially free of its corresponding R enantiomer.

10. A compound of claim 1 wherein $X^1$ is a leaving group, said leaving group is organosulfonyloxy and said organosulfonyloxy is methanesulfonyloxy, benzenesulfonyloxy, p-toluenesulfonyloxy, p-nitrobenzenesulfonyloxy or m-nitrobenzenesulfonyloxy.

11. A compound of claim 10 wherein said organosulfonyloxy is p-toluenesulfonyloxy.

12. A compound of claim 11 wherein said protected amino, for each occurrence, is independently selected from the group consisting of $(C_{1-C_8})$alkylamino, $-NR^3CO(CH_2)_p R^0$, $-NR^3CO_2R^0$ and $-NR^3SO_2(CH_2)_p R^0$;

$R^3$, for each occurrence, is independently H or $(C_1-C_6)$alkyl;

$R^0$, for each occurrence, is independently $(C_1-C_{10})$alkyl, phenyl or phenyl independently substituted by one to three $(C_1-C_4)$alkyl, $(C_1-C_4)$alkoxy or halo; and p is 0, 1 or 2.

13. A compound of claim 12 wherein $R^2$ is H.

14. A compound of claim 13 wherein $R^1$ is amino, $-NR^3CO(C_1-C_{10})$alkyl, $-NR^3CO_2(C_1-C_8)$alkyl or $-NR^3CO(CH_2)_p R^0$.

15. A compound of claim 14 wherein $R^1$ is amino or $-NR^3CO(C_1-C_{10})$alkyl).

16. The compound of claim 15 which is toluene-4-sulfonic acid 2-(6-acetylamino-pyridin-3-yl)-2-hydroxyethyl ester.

17. The R enantiomer of the compound of claim 16, essentially free of its corresponding S enantiomer.

18. The S enantiomer of the compound of claim 16, essentially free of its corresponding R enantiomer.

19. The compound of claim 15 which is N-(5-(2-chloro-1-hydroxyethyl)-1-pyridin-2-yl)-acetamide.

20. The R enantiomer of the compound of claim 19, essentially free of its corresponding S enantiomer.

21. The S enantiomer of the compound of claim 19, essentially free of its corresponding R enantiomer.

22. A compound of claim 1 wherein $X^1$ is a leaving group selected from chloro or iodo.

23. A compound of claim 22 wherein $X^1$ is chloro and said compound is the R enantiomer, essentially free of its corresponding S enantiomer.

24. A compound of claim 22 wherein $X^1$ is chloro and said compound is the S enantiomer, essentially free of its corresponding R enantiomer.

25. A compound of claim 1 wherein $X^1$ is bromo and said compound is the R enantiomer, essentially free of its corresponding S enantiomer.

26. A compound of claim 1 wherein $X^1$ is bromo and said compound is the S enantiomer, essentially free of its corresponding R enantiomer.

27. A compound of the formula

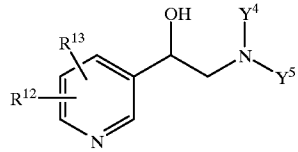

wherein:

$R^{12}$ is selected from the group consisting of nitro and protected amino;

$R^{13}$ is selected from the group consisting of H, fluoro, chloro, $CF_3$, nitro, $(C_1-C_4)$alkyl, $(C_1-C_4)$alkoxy and protected amino;

$Y^4$ is an amine protecting group; and $Y^5$ is

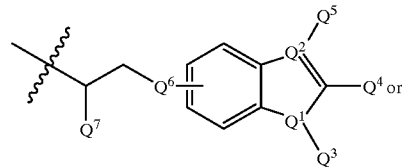

-continued

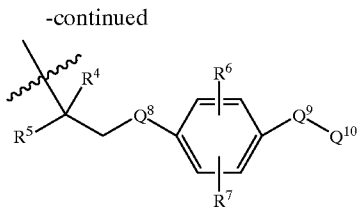

wherein:

$Q^1$ is oxygen, nitrogen or sulfur;

$Q^2$ is carbon or nitrogen;

$Q^3$ is hydrogen, —$(CH_2)_n$-phenyl, -$(C_1-C_{10})$alkyl, —$(CH_2)_n$—$NG^1G^2$, —$(CH_2)_n$—$CO_2G^3$, —$(CH_2)_n$—CO—$NG^1G^2$, —$(CH_2)_n$—$OG^3$, —$(CH_2)_n$—$SO_3G^3$, —$(CH_2)_n$—$SO_2$-$(C_1-C_6)$alkyl, —$(CH_2)_n$—$SO_2NG^1G^2$, or a heterocycle selected from the group consisting of —$(CH_2)_n$-pyridyl, —$(CH_2)_n$-pyrimidyl, —$(CH_2)_n$-pyrazinyl, —$(CH_2)_n$-isoxazolyl, —$(CH_2)_n$-oxazolyl, —$(CH_2)_n$-thiazolyl, —$(CH_2)_n$-(1,2,4-oxadiazolyl), —$(CH_2)_n$-imidazolyl, —$(CH_2)_n$-triazolyl and —$(CH_2)_n$-tetrazolyl;

wherein one of the ring nitrogen atoms of said —$(CH_2)_n$- imidazolyl, —$(CH_2)_n$-triazolyl and —$(CH_2)_n$-tetrazolyl may optionally be substituted by $(C_1-C_8)$ alkyl optionally independently substituted with one or more halo atoms; wherein each of said heterocycles may optionally be substituted on one or more of the ring carbon atoms by one or more substituents independently selected from the group consisting of $(C_1-C_8)$alkyl optionally independently substituted with one or more halo atoms, halo, nitro, cyano, —$(CH_2)_n$—$NG^1G^2$, —$(CH_2)_n$—$CO_2G^3$, —$(CH_2)_n$—CO—$NG^1G^2$, —$(CH_2)_n$—$OG^3$, —$(CH_2)_n$—$SO_3G^3$, —$(CH_2)_n$—$SO_2$-$(C_1-C_6)$alkyl and —$(CH_2)_n$—$SO_2NG^1G^2$;

wherein the phenyl moiety of said —$(CH_2)_n$-phenyl may optionally be substituted with one or more substituents independently selected from the group consisting of $(C_1-C_6)$alkyl optionally independently substituted with one or more halo atoms, hydroxy, $(C_1-C_6)$alkoxy optionally independently substituted with one or more halo atoms, $(C_1-C_6)$alkylthio, fluoro, chloro, bromo, iodo, cyano, nitro, —$(CH_2)_n$—$NG^1G^2$, —$(CH_2)_n$—$CO_2G^3$, —$(CH_2)_n$—CO—$NG^1G^2$, —$(CH_2)_n$—$OG^3$, —$(CH_2)_n$—$SO_3G^3$, —$(CH_2)_n$—$SO_2$-$(C_1-C_6)$alkyl, —$(CH_2)_n$—$SO_2NG^1G^2$; —$(CH_2)_n$—$NG^3$—$SO_2$—$G^3$ and —$(CH_2)_n$—$NG^3$—$SO_2$—$NG^1G^2$;

$Q^4$ is —$(CH_2)_n$—CN, —$(CH_2)_nCO_2G^3$, —$(CH_2)_n$—$SO_3G^3$, —$(CH_2)_n$—$SO_2$-$(C_1-C_6)$alkyl, —$(CH_2)_n$—$SO_2NG^1G^2$, —$(CH_2)_nCH_2OH$, —$(CH_2)_n$—CHO, —$(CH_2)_n$—CO—$G^3$, —$(CH_2)_n$—$CONG^1G^2$, or a heterocycle selected from —$(CH_2)_n$-thiazolyl, —$(CH_2)_n$-oxazolyl, —$(CH_2)_n$-imidazolyl, —$(CH_2)_n$-triazolyl, —$(CH_2)_n$-1,2,4-oxadiazolyl, —$(CH_2)_n$-isoxazolyl, —$(CH_2)_n$-tetrazolyl and —$(CH_2)_n$-pyrazolyl;

wherein one of the ring nitrogen atoms of said —$(CH_2)_n$- imidazolyl, —$(CH_2)_n$-triazolyl and —$(CH_2)_n$-tetrazolyl may optionally be substituted by $(C_1-C_6)$ alkyl optionally independently substituted with one or more halo atoms; wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, —$(CH_2)_n$—CO—$NG^1G^2$, —$(CH_2)_n$—$CO_2G^3$, halo, nitro, cyano, —$(CH_2)_n$—CO—$NG^1G^2$, —$(CH_2)_n$—$OG^3$, —$(CH_2)_n$—$SO_3G^3$, —$(CH_2)_n$—$SO_2$-$(C_1-C_6)$alkyl, or —$(CH_2)_n$—$SO_2NG^1G^2$;

$Q^5$ is hydrogen or $(C_1-C_6)$alkyl optionally independently substituted with one or more halo atoms;

$Q^6$ is a covalent bond, oxygen or sulfur;

$Q^7$ is hydrogen or $(C_1-C_6)$alkyl optionally independently substituted with one or more halo atoms;

$Q^8$ and $Q^9$ are independently a covalent bond, oxygen, sulfur, NH or N-$(C_1-C_6)$alkyl;

$Q^{10}$ is $(CH_2)_mOR^9$, $(CH_2)_nCO_2H$, $(CH_2)_nCOR^{11}$, $(CH_2)_nSO_2NR^9R^{10}$, $(CH_2)_n$—$NR^9SO_2R^8$, $(CH_2)_nP(O)(OR^4)(OR^5)$, $(CH_2)_n$—O—$(CH_2)_nCO_2H$, $(CH_2)_n$—O—$(CH_2)_mCOR^{11}$, $(CH_2)_n$—O—$(CH_2)_mP(O)(OR^4)(OR^5)$, $(CH_2)_n$—O—$(CH_2)_mSO_2NR^9R^{10}$, or $(CH_2)_n$—O—$(CH_2)_m$—$NR^9SO_2R^8$;

$R^4$ and $R^5$ are each independently hydrogen or $(C_1-C_6)$ alkyl; and $R^6$ and $R^7$ are each independently hydrogen, halo, $(C_1-C_6)$alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^6SO_2R^8$, $NR^9COR^{11}$, $NR^9CO_2R^9$ or $OR^9$;

where $G^1$ and $G^2$ for each occurrence are each independently hydrogen, $(C_1-C_6)$alkyl optionally independently substituted with one or more halo, $(C_1-C_8)$alkoxy$(C_1-C_6)$alkyl or $(C_3-C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or $(C_1-C_6)$alkyl;

$R^8$ for each occurrence is independently $(C_1-C_6)$alkyl or $(C_1-C_6)$alkoxy$(C_1-C_6)$alkyl;

$R^9$ and $R^{10}$ are taken separately and, for each occurrence, are independently hydrogen, $(C_1-C_6)$ alkyl, $(C_3-C_8)$cycloalkyl, or $(C_1-C_6)$alkoxy$(C_1-C_6)$ alkyl, or $R^9$ and $R^{10}$ are taken together with the nitrogen atom to which they are attached and form a pyrrolidine, piperidine or morpholine ring wherein said pyrrolidine, piperidine or morpholine may optionally be substituted at any carbon atom by $(C_1-C_4)$alkyl or $(C_1-C_4)$alkoxy;

$R^{11}$ for each occurrence is independently hydrogen, $(C_1-C_6)$alkyl, $(C_1-C_6)$alkoxy, $NR^9R^{10}$, $(C_3-C_8)$ cycloalkyl, or $(C_1-C_6)$alkoxy$(C_1-C_6)$alkyl wherein $R^9$ and $R^{10}$ are as defined above;

m for each occurrence is independently an integer of 1 to 6; and n for each occurrence is independently 0 or an integer of 1 to 6;

racemic mixtures thereof;

R enantiomers thereof, wherein said R enantiomer is essentially free of its corresponding S enantiomer; and S enantiomers thereof, wherein said R enantiomer is essentially free of its corresponding R enantiomer;

provided that:

(1) when $Q^9$ is O or S then n is not 0;

(2) when $Q^1$ is oxygen or sulfur then $Q^3$ is absent; and (3) when $Q^2$ is nitrogen then $Q^5$ is absent.

28. A compound of claim 27 wherein $Y^4$ is an amine protecting group selected from the group consisting of benzyl, $COR^{14}$, $CO_2R^{14}$ and $SO_2R^{14}$; and $R^{14}$, for each occurrence, is independently $(C_1–C_{10})$alkyl, phenyl or benzyl; wherein said phenyl and benzyl are independently optionally substituted by one to three $(C_1–C_4)$alkyl, $(C_1–C_4)$alkoxy or halo.

29. A compound of claim 28 wherein $Y^5$ is

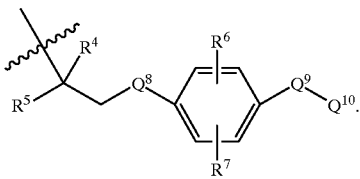

30. A compound of claim 29 wherein $R^{13}$ is H and $R^{12}$ is protected amino; said protected amino is independently selected from the group consisting of $(C_1–C_8)$alkylamino, —$NR^3CO(CH_2)_pR^0$, —$NR^3CO_2R^0$ and —$NR^3SO_2(CH_2)_pR^0$;

$R^3$ is independently H or $(C_1–C_6)$alkyl;

$R^0$ is independently $(C_1–C_{10})$alkyl, phenyl or phenyl independently substituted by one to three $(C_1–C_4)$alkyl, $(C_1–C_4)$alkoxy or halo; and p is 0, 1 or 2.

31. A compound of claim 30 wherein said protected amino is $NR^3CO(CH_2)_pR^0$; $R^3$ is H; $R^0$ is $CH_3$; and p is 0.

32. A compound of claim 31 wherein $R^4$, $R^5$, $R^6$ and $R^7$ are each hydrogen; $Q^8$ is oxygen; $Q^9$ is a covalent bond; and $Q^{10}$ is $(CH_2)_mCONR^9R^{10}$.

33. A compound of claim 32 wherein $Y^4$ is t-butyloxycarbonyl; m is 1; $R^9$ is H; and $R^{10}$ is methyl.

34. A compound of claim 33 of the formula

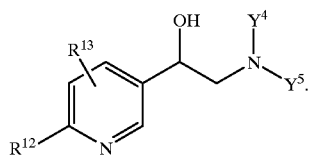

35. A compound of claim 34 having R stereochemistry.

36. The compound of claim 35 which is N-methyl 4-(2-(2-(2-acetylaminopyridin-5-yl)-2-(R)-hydroxyethyl-N-tert-butyloxycarbonylamino)-ethoxy)-phenylacetamide.

37. A process for preparing a compound of the formula

VI

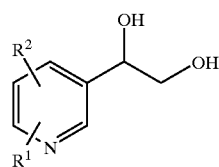

wherein:

$R^1$ is selected from the group consisting of nitro, amino and protected amino; and $R^2$ is selected from the group consisting of H, fluoro, chloro, $CF_3$, nitro, $(C_1–C_4)$alkyl, $(C_1–C_4)$alkoxy, amino and protected amino comprising reacting a compound of the formula

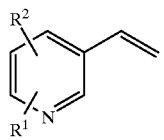

V wherein $R^1$ and $R^2$ are as defined above, with a catalyst comprising an osmium (VIII) oxide or an osmium salt and an auxiliary oxidizing agent in a reaction inert solvent.

38. A process of claim 37 additionally comprising reacting said compound of formula (V) with said osmium (VIII) oxide or said osmium salt in the presence of a chiral auxiliary ligand and an auxiliary base.

39. A process of claim 38 wherein said chiral auxiliary ligand is $(DHQD)_2PHAL$.

40. A process of claim 39 wherein said compound of formula (VI) has an R configuration at the 1-position of the 5-ethyl group, said compound being essentially free of its corresponding S enantiomer.

41. A process of claim 40 wherein $R^1$ is acetylamino and $R^2$ is H.

42. A process of claim 38 wherein said chiral auxiliary ligand is $(DHQ)_2PHAL$.

43. A process of claim 42 wherein said compound of formula (VI) has an S configuration at the 1-position of the 5-ethyl group, said compound being essentially free of its corresponding R enantiomer.

44. A process of claim 43 wherein $R^1$ is acetylamino and $R^2$ is H.

45. A process for preparing a compound of the formula (I),

I

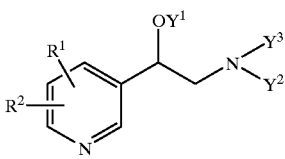

and the racemic-enantiomeric mixtures and optical isomers of said compounds comprising:

(a) reacting a compound of the formula

VI

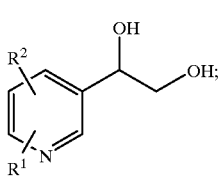

with an organosulfonyl chloride and a suitable base in a reaction inert solvent to form a compound of the formula

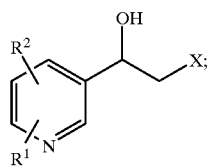

(b) reacting said compound of formula II with a non-nucleophilic base in a reaction inert solvent to form a compound of the formula (III)

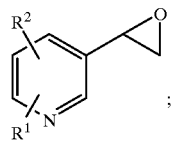

and (c) reacting said compound of formula (III) with a base and $HNY^2Y^3$ to form said compound of formula (I);

wherein:
- $R^1$ is selected from the group consisting of nitro, amino and protected amino;
- $R^2$ is selected from the group consisting of H, fluoro, chloro, $CF_3$, nitro, $(C_1-C_4)$alkyl, $(C_1-C_4)$alkoxy, amino and protected amino; and
- Y is Br, I or trifluoromethanesulfonyloxy; and
- X is organosulfonyloxy;
- $Y^1$ and $Y^3$ are H;
- $Y^2$ is

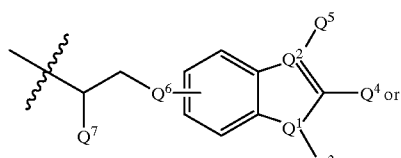

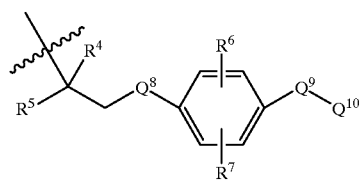

wherein:
- $Q^1$ is oxygen, nitrogen or sulfur;
- $Q^2$ is carbon or nitrogen;
- $Q^3$ is hydrogen, $-(CH_2)_n$-phenyl, $-(C_1-C_{10})$alkyl, $-(CH_2)_n-NG^1G^2$, $-(CH_2)_n-CO_2G^3$, $-(CH_2)_n-CO-NG^1G^2$, $-(CH_2)_n-OG^3$, $-(CH_2)_n-SO_3G^3$, $-(CH_2)_n-SO_2-(C_1-C_6)$alkyl, $-(CH_2)_n-SO_2NG^1G^2$, or a heterocycle selected from the group consisting of $-(CH_2)_n$-pyridyl, $-(CH_2)_n$-pyrimidyl, $-(CH_2)_n$-pyrazinyl, $-(CH_2)_n$-isoxazolyl, $-(CH_2)_n$-oxazolyl, $-(CH_2)_n$-thiazolyl, $-(CH_2)_n$-(1,2,4-oxadiazolyl), $-(CH_2)_n$-imidazolyl, $-(CH_2)_n$-triazolyl and $-(CH_2)_n$-tetrazolyl;
- wherein one of the ring nitrogen atoms of said $-(CH_2)_n$-imidazolyl, $-(CH_2)_n$-triazolyl and $-(CH_2)_n$-tetrazolyl may optionally be substituted by $(C_1-C_8)$alkyl optionally independently substituted with one or more halo atoms; wherein each of said heterocycles may optionally be substituted on one or more of the ring carbon atoms by one or more substituents independently selected from the group consisting of $(C_1-C_8)$alkyl optionally independently substituted with one or more halo atoms, halo, nitro, cyano, $-(CH_2)_n-NG^1G^2$, $-(CH_2)_n-CO_2G^3$, $-(CH_2)_n-CO-NG^1G^2$, $-(CH_2)_n-OG^3$, $-(CH_2)_n-SO_3G^3$, $-(CH_2)_n-SO_2-(C_1-C_6)$alkyl and $-(CH_2)_n-SO_2NG^1G^2$;
- wherein the phenyl moiety of said $-(CH_2)_n$-phenyl may optionally be substituted with one or more substituents independently selected from the group consisting of $(C_1-C_6)$alkyl optionally independently substituted with one or more halo atoms, hydroxy, $(C_1-C_6)$alkoxy optionally independently substituted with one or more halo atoms, $(C_1-C_6)$alkylthio, fluoro, chloro, bromo, iodo, cyano, nitro, $-(CH_2)_n-NG^1G^2$, $-(CH_2)_n-CO_2G^3$, $-(CH_2)_n-CO-NG^1G^2$, $-(CH_2)_n-OG^3$, $-(CH_2)_n-SO_3G^3$, $-(CH_2)_n-SO_2-(C_1-C_6)$alkyl, $-(CH_2)_n-SO_2NG^1G^2$; $-(CH_2)_n-NG^3-SO_2-G^3$ and $-(CH_2)_n-NG^3-SO_2-NG^1G^2$;
- $Q^4$ is $-(CH_2)_n-CN$, $-(CH_2)_nCO_2G^3$, $-(CH_2)_n-SO_3G^3$, $-(CH_2)_n-SO_2-(C_1-C_6)$alkyl, $-(CH_2)_n-SO_2NG^1G^2$, $-(CH_2)_nCH_2OH$, $-(CH_2)_n-CHO$, $-(CH_2)_n-CO-G^3$, $-(CH_2)_n-CONG^1G^2$, or a heterocycle selected from $-(CH_2)_n$-thiazolyl, $-(CH_2)_n$-oxazolyl, $-(CH_2)_n$-imidazolyl, $-(CH_2)_n$-triazolyl, $-(CH_2)_n$-1,2,4-oxadiazolyl, $-(CH_2)_n$-isoxazolyl, $-(CH_2)_n$-tetrazolyl and $-(CH_2)_n$-pyrazolyl;
- wherein one of the ring nitrogen atoms of said $-(CH_2)_n$-imidazolyl, $-(CH_2)_n$-triazolyl and $-(CH_2)_n$-tetrazolyl may optionally be substituted by $(C_1-C_6)$alkyl optionally independently substituted with one or more halo atoms; wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, $-(CH_2)_n-CO-NG^1G^2$, $-(CH_2)_n-CO_2G^3$, halo, nitro, cyano, $-(CH_2)_n-CO-NG^1G^2$, $-(CH_2)_n-OG^3$, $-(CH_2)_n-SO_3G^3$, $-(CH_2)_n-SO_2-(C_1-C_6)$alkyl, or $-(CH_2)_n-SO_2NG^1G^2$;
- $Q^5$ is hydrogen or $(C_1-C_6)$alkyl optionally independently substituted with one or more halo atoms;
- $Q^6$ is a covalent bond, oxygen or sulfur;
- $Q^7$ is hydrogen or $(C_1-C_6)$alkyl optionally independently substituted with one or more halo atoms;
- $Q^8$ and $Q^9$ are independently a covalent bond, oxygen, sulfur, NH or N-$(C_1-C_6)$alkyl;
- $Q^{10}$ is $(CH_2)_mOR^9$, $(CH_2)_nCO_2H$, $(CH_2)_nCOR^{11}$, $(CH_2)_nSO_2NR^9R^{10}$, $(CH_2)_n-NR^9SO_2R^8$, $(CH_2)_nP(O)(OR^4)(OR^5)$, $(CH_2)_n-O-(CH_2)_mCO_2H$, $(CH_2)_n-O-(CH_2)_mCOR^{11}$, $(CH_2)_n-O-(CH_2)_mP(O)(OR^4)(OR^5)$, $(CH_2)_n-O-(CH_2)_mSO_2NR^9R^{10}$, or $(CH_2)_n-O-(CH_2)_m-NR^9SO_2R^8$;
- $R^4$ and $R^5$ are each independently hydrogen or $(C_1-C_6)$alkyl; and
- $R^6$ and $R^7$ are each independently hydrogen, halo, $(C_1-C_6)$alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^9SO_2R^8$, $NR^9COR^{11}$, $NR^9CO_2R^9$ or $OR^9$;

where $G^1$ and $G^2$ for each occurrence are each independently hydrogen, $(C_1-C_6)$alkyl optionally independently substituted with one or more halo, $(C_1-C_8)$alkoxy$(C_1-C_6)$alkyl or $(C_3-C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or $(C_1-C_6)$alkyl;

$R^8$ for each occurrence is independently $(C_1-C_6)$alkyl or $(C_1-C_6)$alkoxy$(C_1-C_6)$alkyl;

$R^9$ and $R^{10}$ for each occurrence are independently hydrogen, $(C_1-C_6)$alkyl, $(C_3-C_8)$cycloalkyl, or $(C_1-C_6)$alkoxy$(C_1-C_6)$alkyl;

$R^{11}$ for each occurrence is independently hydrogen, $(C_1-C_6)$alkyl, $(C_1-C_6)$alkoxy, $NR^9R^{10}$, $(C_3-C_8)$cycloalkyl, or $(C_1-C_6)$alkoxy$(C_1-C_6)$alkyl wherein $R^9$ and $R^{10}$ are as defined above;

m for each occurrence is independently an integer of 1 to 6; and n for each occurrence is independently 0 or an integer of 1 to 6;

provided that:

(1) when $Q^9$ is O or S then n is not 0;

(2) when $Q^1$ is oxygen or sulfur then $Q^3$ is absent; and (3) when $Q^2$ is nitrogen then $Q^5$ is absent.

46. A process of claim 45 wherein said organosulfonyloxy is methanesulfonyloxy, benzenesulfonyloxy, p-toluenesulfonyloxy, p-nitrobenzenesulfonyloxy or m-nitrobenzenesulfonyloxy.

47. A process for preparing a compound of formula

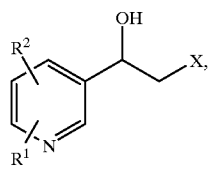

II wherein: $R^1$ is selected from the group consisting of nitro, amino and protected amino; $R^2$ is selected from the group consisting of H, fluoro, chloro, $CF_3$, nitro, $(C_1-C_4)$alkyl, $(C_1-C_4)$alkoxy, amino and protected amino; and X is organosulfonyloxy, comprising:

reacting a compound of the formula

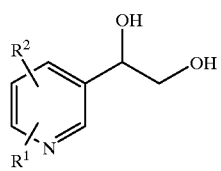

VI wherein $R^1$ and $R^2$ are as defined above, with an organosulfonyl chloride and a suitable base in a reaction inert solvent.

48. A process for preparing a compound of the formula

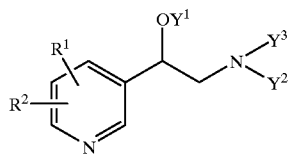

I and the racemic-enantiomeric mixtures and optical isomers of said compounds comprising:

(a) reacting a compound of the formula

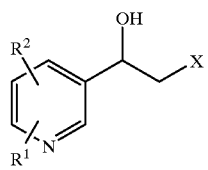

II with a non-nucleophilic base in a reaction inert solvent to form a compound of the formula (III)

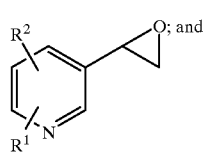

III (b) reacting said compound of formula (III) with a base and $HNY^2Y^3$ to form said compound of formula (I), wherein:

$R^1$ is selected from the group consisting of nitro, amino and protected amino;

$R^2$ is selected from the group consisting of H, fluoro, chloro, $CF_3$, nitro, $(C_1-C_4)$alkyl, $(C_1-C_4)$alkoxy, amino and protected amino;

X is an organosulfonyloxy group;

$Y^1$ and $Y^3$ are H;

$Y^2$ is

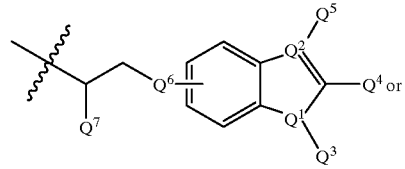

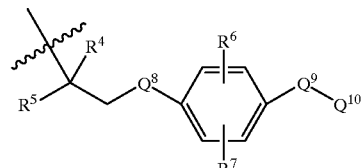

wherein:

$Q^1$ is oxygen, nitrogen or sulfur;

$Q^2$ is carbon or nitrogen;

$Q^3$ is hydrogen, $-(CH_2)_n$-phenyl, $-(C_1-C_{10})$alkyl, $-(CH_2)_n-NG^1G^2$, $-(CH_2)_n-CO_2G^3$, $-(CH_2)_n-$ CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl, —(CH$_2$)$_n$—SO$_2$NG$^1$G$^2$, or a heterocycle selected from the group consisting of —(CH$_2$)$_n$-pyridyl, —(CH$_2$)$_n$-pyrimidyl, —(CH$_2$)$_n$-pyrazinyl, —(CH$_2$)$_n$-isoxazolyl, —(CH$_2$)$_n$-oxazolyl, —(CH$_2$)$_n$-thiazolyl, —(CH$_2$)$_n$-(1,2,4-oxadiazolyl), —(CH$_2$)$_n$-imidazolyl, —(CH$_2$)$_n$-triazolyl and —(CH$_2$)$_n$-tetrazolyl;
  wherein one of the ring nitrogen atoms of said —(CH$_2$)$_n$-imidazolyl, —(CH$_2$)$_n$-triazolyl and —(CH$_2$)$_n$-tetrazolyl may optionally be substituted by (C$_1$–C$_8$)alkyl optionally independently substituted with one or more halo atoms; wherein each of said heterocycles may optionally be substituted on one or more of the ring carbon atoms by one or more substituents independently selected from the group consisting of (C$_1$–C$_8$)alkyl optionally independently substituted with one or more halo atoms, halo, nitro, cyano, —(CH$_2$)$_n$—NG$^1$G$^2$, —(CH$_2$)$_n$—CO$_2$G$^3$, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl and —(CH$_2$)$_n$—SO$_2$NG$^1$G$^2$;
  wherein the phenyl moiety of said —(CH$_2$)$_n$-phenyl may optionally be substituted with one or more substituents independently selected from the group consisting of (C$_1$–C$_6$)alkyl optionally independently substituted with one or more halo atoms, hydroxy, (C$_1$–C$_6$)alkoxy optionally independently substituted with one or more halo atoms, (C$_1$–C$_6$)alkylthio, fluoro, chloro, bromo, iodo, cyano, nitro, —(CH$_2$)$_n$—NG$^1$G$^2$, —(CH$_2$)$_n$—CO$_2$G$^3$, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl, —(CH$_2$)$_n$—SO$_2$NG$^1$G$^2$; —(CH$_2$)$_n$—NG$^3$—SO$_2$—G$^3$ and —(CH$_2$)$_n$—NG$^3$—SO$_2$—NG$^1$G$^2$;

Q$^4$ is —(CH$_2$)$_n$—CN, —(CH$_2$)$_n$CO$_2$G$^3$, —(CH$_2$)$_n$—SO$_3$G$^3$, —(CH$_2$)$_n$—SO$_2$-(C$_1$–C$_6$)alkyl, —(CH$_2$)$_n$—SO$_2$NG$^1$G$^2$, —(CH$_2$)$_n$CH$_2$OH, —(CH$_2$)$_n$—CHO, —(CH$_2$)$_n$—CO—G$^3$, —(CH$_2$)$_n$—CONG$^1$G$^2$, or a heterocycle selected from —(CH$_2$)$_n$-thiazolyl, —(CH$_2$)$_n$-oxazolyl, —(CH$_2$)$_n$-imidazolyl, —(CH$_2$)$_n$-triazolyl, —(CH$_2$)$_n$-1,2,4-oxadiazolyl, —(CH$_2$)$_n$-isoxazolyl, —(CH$_2$)$_n$-tetrazolyl and —(CH$_2$)$_n$-pyrazolyl;
  wherein one of the ring nitrogen atoms of said —(CH$_2$)$_n$-imidazolyl, —(CH$_2$)$_n$-triazolyl and —(CH$_2$)$_n$-tetrazolyl may optionally be substituted by (C$_1$–C$_6$)alkyl optionally independently substituted with one or more halo atoms; wherein each of said heterocycles may optionally be substituted on one or more of the ring carbon atoms by one or more substituents independently selected from the group consisting of hydrogen, (C$_1$–C$_6$)alkyl optionally independently substituted with one or more halo atoms, —(CH$_2$)$_n$—CO—NG$^1$G$^2$, —(CH$_2$)$_n$—CO$_2$G$^3$, halo, nitro, cyano, —(CH$_2$)$_n$—CO—NG$^1$G$^2$, —(CH$_2$)$_n$—OG$^3$, —(CH$_2$)$_n$—SO$_3$G$^3$, —(CH$_2$)$_n$—SO$_2$-(C$_1$–C$_6$)alkyl, or —(CH$_2$)$_n$—SO$_2$NG$^1$G$^2$;

Q$^5$ is hydrogen or (C$_1$–C$_6$)alkyl optionally independently substituted with one or more halo atoms;

Q$^6$ is a covalent bond, oxygen or sulfur;

Q$^7$ is hydrogen or (C$_1$–C$_6$)alkyl optionally independently substituted with one or more halo atoms;

Q$^8$ and Q$^9$ are independently a covalent bond, oxygen, sulfur, NH or N-(C$_1$–C$_6$)alkyl;

Q$^{10}$ is (CH$_2$)$_m$OR$^9$, (CH$_2$)$_n$CO$_2$H, (CH$_2$)$_n$COR$^{11}$, (CH$_2$)$_n$SO$_2$NR$^9$R$^{10}$, (CH$_2$)$_n$—NR$^9$SO$_2$R$^8$, (CH$_2$)$_n$P(O)(OR$^4$)(OR$^5$), (CH$_2$)$_n$—O—(CH$_2$)$_m$CO$_2$H, (CH$_2$)$_n$—O—(CH$_2$)$_m$COR$^{11}$, (CH$_2$)$_n$—O—(CH$_2$)$_m$P(O)(OR$^4$)(OR$^5$), (CH$_2$)$_n$—O—(CH$_2$)$_m$SO$_2$NR$^9$R$^{10}$, or (CH$_2$)$_n$—O—(CH$_2$)$_m$—NR$^9$SO$_2$R$^8$;

R$^4$ and R$^5$ are each independently hydrogen or (C$_1$–C$_6$)alkyl; and

R$^6$ and R$^7$ are each independently hydrogen, halo, (C$_1$–C$_6$)alkyl, nitro, cyano, trifluoromethyl, SO$_2$R$^8$, SO$_2$NR$^9$R$^{10}$, NR$^9$R$^{10}$, COR$^{11}$, CO$_2$R$^9$, (C$_1$–C$_6$)alkoxy, NR$^6$SO$_2$R$^8$, NR$^9$COR$^{11}$, NR$^9$CO$_2$R$^9$ or OR$^9$;
  where G$^1$ and G$^2$ for each occurrence are each independently hydrogen, (C$_1$–C$_6$)alkyl optionally independently substituted with one or more halo, (C$_1$–C$_8$)alkoxy(C$_1$–C$_6$)alkyl or (C$_3$–C$_8$)cycloalkyl, or G$^1$ and G$^2$ together with the nitrogen to which they are attached form a saturated heterocyclic ring having from 3 to 7 carbon atoms wherein one of said carbon atoms may optionally be replaced by oxygen, nitrogen or sulfur;
  G$^3$ for each occurrence is independently hydrogen or (C$_1$–C$_6$)alkyl;
  R$^8$ for each occurrence is independently (C$_1$–C$_6$)alkyl or (C$_1$–C$_6$)alkoxy(C$_1$–C$_6$)alkyl;
  R$^9$ and R$^{10}$ for each occurrence are independently hydrogen, (C$_1$–C$_6$)alkyl, (C$_3$–C$_8$)cycloalkyl, or (C$_1$–C$_6$)alkoxy(C$_1$–C$_6$)alkyl;
  R$^{11}$ for each occurrence is independently hydrogen, (C$_1$–C$_6$)alkyl, (C$_1$–C$_6$)alkoxy, NR$^9$R$^{10}$, (C$_3$–C$_8$)cycloalkyl, or (C$_1$–C$_6$)alkoxy(C$_1$–C$_6$)alkyl wherein R$^9$ and R$^{10}$ are as defined above;
  m for each occurrence is independently an integer of 1 to 6; and
  n for each occurrence is independently 0 or an integer of 1 to 6;
provided that:
  (1) when Q$^9$ is O or S then n is not 0;
  (2) when Q$^1$ is oxygen or sulfur then Q$^3$ is absent; and
  (3) when Q$^2$ is nitrogen then Q$^5$ is absent.

49. A process of claim 48 wherein said organosulfonyloxy is methanesulfonyloxy, benzenesulfonyloxy, p-toluenesulfonyloxy, p-nitrobenzenesulfonyloxy or m-nitrobenzenesulfonyloxy.

50. A process for preparing a compound of the formula (I),

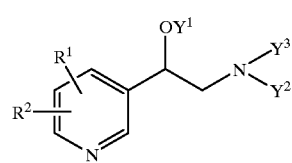

I and the racemic-enantiomeric mixtures and optical isomers of said compounds comprising:
  (a) reacting a compound of the formula

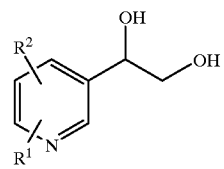

VI with an organosulfonyl chloride and a suitable base in a reaction inert to form a compound of the formula

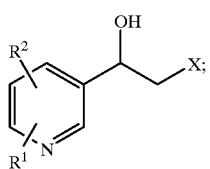

II (b) reacting said compound of formula (II) with a chlorinating agent in a reaction inert solvent to form a compound of the formula (VII)

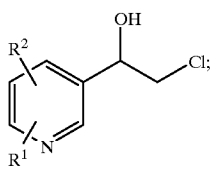

VII (c) reacting said compound of formula (VII) with a non-nucleophilic base in a reaction inert to form a compound of the formula (III)

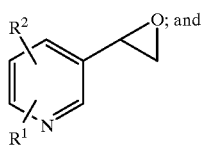

III (d) reacting said compound of formula (III) with a base and $HNY^2Y^3$ to form said compound of formula (I);

wherein:
$R^1$ is selected from the group consisting of nitro, amino and protected amino;
$R^2$ is selected from the group consisting of H, fluoro, chloro, $CF_3$, nitro, $(C_1-C_4)$alkyl, $(C_1-C_4)$alkoxy, amino and protected amino; and
X is organosulfonyloxy;
$Y^1$ and $Y^3$ are H;
$Y^2$ is

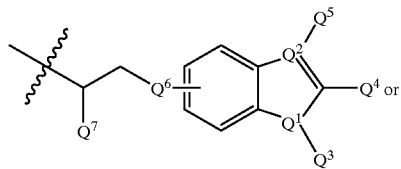
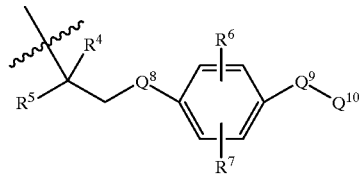

wherein:
$Q^1$ is oxygen, nitrogen or sulfur;
$Q^2$ is carbon or nitrogen;
$Q^3$ is hydrogen, $—(CH_2)_n$-phenyl, $-(C_1-C_{10})$alkyl, $—(CH_2)_n—NG^1G^2$, $—(CH_2)_n—CO_2G^3$, $—(CH_2)_n—CO—NG^1G^2$, $—(CH_2)_n—OG^3$, $—(CH_2)_n—SO_3G^3$, $—(CH_2)_n—SO_2-(C_1-C_6)$alkyl, $—(CH_2)_n—SO_2NG^1G^2$, or a heterocycle selected from the group consisting of $—(CH_2)_n$-pyridyl, $—(CH_2)_n$-pyrimidyl, $—(CH_2)_n$-pyrazinyl, $—(CH_2)_n$-isoxazolyl, $—(CH_2)_n$-oxazolyl, $—(CH_2)_n$-thiazolyl, $—(CH_2)_n$-(1,2,4-oxadiazolyl), $—(CH_2)_n$-imidazolyl, $—(CH_2)_n$-triazolyl and $—(CH_2)_n$-tetrazolyl;

wherein one of the ring nitrogen atoms of said $—(CH_2)_n$-imidazolyl, $—(CH_2)_n$-triazolyl and $—(CH_2)_n$-tetrazolyl may optionally be substituted by $(C_1-C_8)$alkyl optionally independently substituted with one or more halo atoms; wherein each of said heterocycles may optionally be substituted on one or more of the ring carbon atoms by one or more substituents independently selected from the group consisting of $(C_1-C_8)$alkyl optionally independently substituted with one or more halo atoms, halo, nitro, cyano, $—(CH_2)_n—NG^1G^2$, $—(CH_2)_n—CO_2G^3$, $—(CH_2)_n—CO—NG^1G^2$, $—(CH_2)_n—OG^3$, $—(CH_2)_n—SO_3G^3$, $—(CH_2)_n—SO_2-(C_1-C_6)$alkyl and $—(CH_2)_n—SO_2NG^1G^2$;

wherein the phenyl moiety of said $—(CH_2)_n$-phenyl may optionally be substituted with one or more substituents independently selected from the group consisting of $(C_1-C_6)$alkyl optionally independently substituted with one or more halo atoms, hydroxy, $(C_1-C_6)$alkoxy optionally independently substituted with one or more halo atoms, $(C_1-C_6)$alkylthio, fluoro, chloro, bromo, iodo, cyano, nitro, $—(CH_2)_n—NG^1G^2$, $—(CH_2)_n—CO_2G^3$, $—(CH_2)_n—CO—NG^1G^2$, $(CH_2)_n—OG^3$, $—(CH_2)_n—SO_3G^3$, $—(CH_2)_n—SO_2-(C_1-C_6)$alkyl, $—(CH_2)_n—SO_2NG^1G^2$; $—(CH_2)_n—NG^3—SO_2—G^3$ and $—(CH_2)_n—NG^3—SO_2—NG^1G^2$;

$Q^4$ is $—(CH_2)_n—CN$, $—(CH_2)_nCO_2G^3$, $—(CH_2)_n—SO_3G^3$, $—(CH_2)_n—SO_2-(C_1-C_6)$alkyl, $—(CH_2)_n—SO_2NG^1G^2$, $—(CH_2)_nCH_2OH$, $—(CH_2)_n—CHO$, $—(CH_2)_n—CO—G^3$, $—(CH_2)_n—CONG^1G^2$, or a heterocycle selected from $—(CH_2)_n$-thiazolyl, $—(CH_2)_n$-oxazolyl, $—(CH_2)_n$-imidazolyl, $—(CH_2)_n$-triazolyl, $—(CH_2)_n$-1,2,4-oxadiazolyl, $—(CH_2)_n$-isoxazolyl, $—(CH_2)_n$-tetrazolyl and $—(CH_2)_n$-pyrazolyl;

wherein one of the ring nitrogen atoms of said $—(CH_2)_n$-imidazolyl, $—(CH_2)_n$-triazolyl and $—(CH_2)_n$-tetrazolyl may optionally be substituted by $(C_1-C_6)$alkyl optionally independently substituted with one or more halo atoms; wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, $—(CH_2)_n—CO—NG^1G^2$, $—(CH_2)_n—CO_2G^3$, halo, nitro, cyano, $—(CH_2)_n—CO—NG^1G^2$, $—(CH_2)_n—OG^3$, $—(CH_2)_n—SO_3G^3$, $—(CH_2)_n—SO_2-(C_1-C_6)$alkyl, or $—(CH_2)_n—SO_2NG^1G^2$;

$Q^5$ is hydrogen or $(C_1-C_6)$alkyl optionally independently substituted with one or more halo atoms;

$Q^6$ is a covalent bond, oxygen or sulfur;

$Q^7$ is hydrogen or $(C_1-C_6)$alkyl optionally independently substituted with one or more halo atoms;

$Q^8$ and $Q^9$ are independently a covalent bond, oxygen, sulfur, NH or N-$(C_1-C_6)$alkyl;

$Q^{10}$ is $(CH_2)_mOR^9$, $(CH_2)_nCO_2H$, $(CH_2)_nCOR^{11}$, $(CH_2)_nSO_2NR^9R^{10}$, $(CH_2)_n—NR^9SO_2R^8$, $(CH_2)_nP(O)(OR^4)$ (OR⁵), $(CH_2)_n$—O—$(CH_2)_mCO_2H$, $(CH_2)_n$—O—$(CH_2)_mCOR^{11}$, $(CH_2)_n$—O—$(CH_2)_mP(O)(OR^4)(OR^5)$, $(CH_2)_n$—O—$(CH_2)_mSO_2NR^9R^{10}$, or $(CH_2)_n$—O—$(CH_2)_m$—$NR^9SO_2R^8$;

$R^4$ and $R^5$ are each independently hydrogen or $(C_1-C_6)$alkyl; and $R^6$ and $R^7$ are each independently hydrogen, halo, $(C_1-C_6)$alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^9SO_2R^8$, $NR^9COR^{11}$, $NR^9CO_2R^9$ or $OR^9$;

where $G^1$ and $G^2$ for each occurrence are each independently hydrogen, $(C_1-C_6)$alkyl optionally independently substituted with one or more halo, $(C_1-C_8)$alkoxy$(C_1-C_6)$alkyl or $(C_3-C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or $(C_1-C_6)$alkyl;

$R^8$ for each occurrence is independently $(C_1-C_6)$alkyl or $(C_1-C_6)$alkoxy$(C_1-C_6)$alkyl;

$R^9$ and $R^{10}$ for each occurrence are independently hydrogen, $(C_1-C_6)$alkyl, $(C_3-C_8)$cycloalkyl, or $(C_1-C_6)$alkoxy$(C_1-C_6)$alkyl;

$R^{11}$ for each occurrence is independently hydrogen, $(C_1-C_6)$alkyl, $(C_1-C_6)$alkoxy, $NR^9R^{10}$, $(C_3-C_8)$ cycloalkyl, or $(C_1-C_6)$alkoxy$(C_1-C_6)$alkyl wherein $R^9$ and $R^{10}$ are as defined above;

m for each occurrence is independently an integer of 1 to 6; and n for each occurrence is independently 0 or an integer of 1 to 6;

provided that:

(1) when $Q^9$ is O or S then n is not 0;

(2) when $Q^1$ is oxygen or sulfur then $Q^3$ is absent; and (3) when $Q^2$ is nitrogen then $Q^5$ is absent.

51. A process of claim 50 wherein said chlorinating agent is lithium chloride and said organosulfonyloxy is selected from the group selected consisting of methanesulfonyloxy, benzenesulfonyloxy, p-toluenesulfonyloxy, p-nitrobenzenesulfonyloxy or m-nitrobenzenesulfonyloxy.

52. A process of claim 48 wherein prior to said step (a), said compound of formula (II) is prepared by reacting a compound of the formula

VI

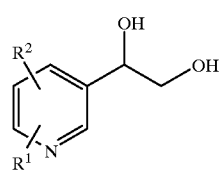

with an organosulfonyl chloride and a suitable base in a reaction inert solvent.

53. A process of claim 52 wherein said organosulfonyloxy is methanesulfonyloxy, benzenesulfonyloxy, p-toluenesulfonyloxy, p-nitrobenzenesulfonyloxy or m-nitrobenzenesulfonyloxy.

54. A process for preparing a compound of the formula (XIII)

XIII

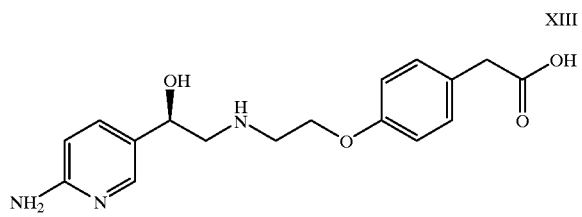

comprising reacting a compound of the formula (XIV)

XIV

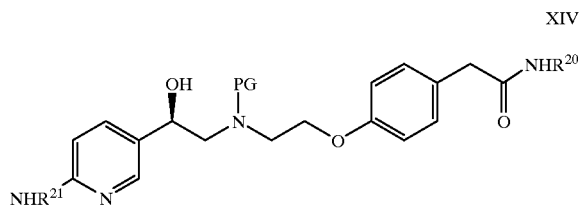

wherein:

PG is an amine protecting group;

$R^{20}$ is $(C_1-C_8)$alkyl;

$R^{21}$ is selected from the group consisting of $(C_1-C_8)$alkyl, $COR^{22}$, $CO_2R^{22}$ and $SO_2R^{22}$; and $R^{22}$ is $(C_1-C_8)$alkyl with an aqueous acid.

55. A process of claim 54 wherein said amine protecting group is selected from the group consisting of $COR^{22}$, $CO_2R^{22}$ and $SO_2R^{22}$; and $R^{22}$ is $(C_1-C_8)$alkyl.

56. A process of claim 55 wherein said compound of formula XIV is N-methyl 4-(2-(2-(2-acetylaminopyridin-5-yl)-2-(R)-hydroxyethyl-N-tert-butyloxycarbonylamino)-ethoxy)-phenylacetamide.

57. A process for preparing a compound of the formula

XIII

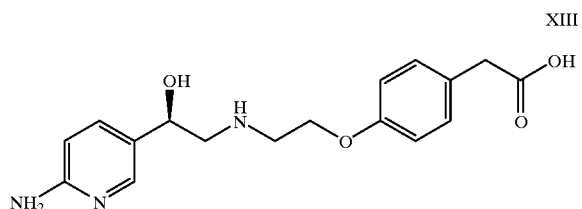

comprising:

(a) reacting a compound of the formula

XV

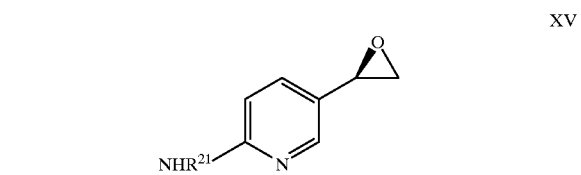

wherein $R^{21}$ is $COR^{22}$ and $R^{22}$ is $(C_1-C_8)$alkyl with a compound of the formula

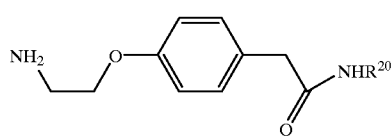

wherein $R^{20}$ is $(C_1–C_8)$alkyl in a reaction inert solvent to form a compound of the formula

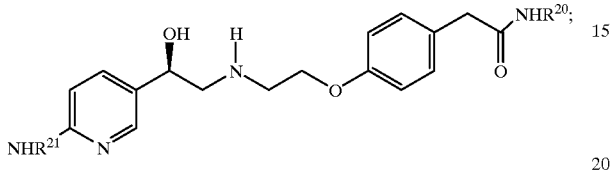

(b) reacting said compound of formula (XVII) with an acid anhydride, a dicarbonate or an acid chloride to form a compound of the formula

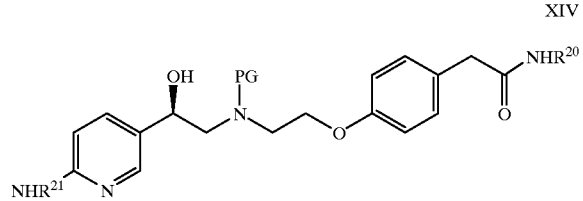

wherein $R^{20}$ and $R^{21}$ are as defined above and PG is an amine protecting group; and (c) reacting said compound of formula (XIV) with an aqueous acid to form said compound of formula (XIII).

58. A process of claim 57 wherein said amine protecting group is selected from the group consisting of $COR^{22}$ and $CO_2R^{22}$; and $R^{22}$ is $(C_1–C_8)$alkyl.

59. A process of claim 58 wherein said compound of formula (XVII) is reacted with a dicarbonate.

60. A process of claim 59 wherein $R^{21}$ is acetyl, $R^{20}$ is methyl and PG is tert-butyloxycarbonyl.

* * * * *